US011166871B2

(12) United States Patent
Olkowski et al.

(10) Patent No.: US 11,166,871 B2
(45) Date of Patent: *Nov. 9, 2021

(54) EYELID CARE APPLIANCE

(71) Applicant: NuSight Medical, Rancho Santa Fe, CA (US)

(72) Inventors: John David Olkowski, Honolulu, HI (US); Kirk Keoni Olkowski, Honolulu, HI (US)

(*) Notice: Subject to any disclaimer, the term of this patent is extended or adjusted under 35 U.S.C. 154(b) by 412 days.

This patent is subject to a terminal disclaimer.

(21) Appl. No.: 16/402,143

(22) Filed: May 2, 2019

(65) Prior Publication Data
US 2019/0262224 A1    Aug. 29, 2019

Related U.S. Application Data

(63) Continuation of application No. 14/588,392, filed on Dec. 31, 2014, now Pat. No. 10,314,763.
(Continued)

(51) Int. Cl.
*A61H 7/00* (2006.01)
*A61B 3/14* (2006.01)
(Continued)

(52) U.S. Cl.
CPC .............. *A61H 23/02* (2013.01); *A46B 9/028* (2013.01); *A46B 13/008* (2013.01); *A46B 13/02* (2013.01); *A61F 9/00772* (2013.01); *A61H 7/005* (2013.01); *A61H 35/02* (2013.01); *G09B 19/003* (2013.01); *G09B 19/0076* (2013.01); *A46B 2200/102* (2013.01); *A61H 2201/0153* (2013.01); *A61H 2201/0188* (2013.01); *A61H 2201/0207* (2013.01); *A61H 2201/0214* (2013.01); *A61H 2201/10* (2013.01);
(Continued)

(58) Field of Classification Search
CPC .............. A61H 35/02; A61H 2205/024; A61F 2007/0004; A61F 9/00772; A61M 2210/0612; A61C 17/32; A61B 3/12; A61B 3/14; A61B 3/145
See application file for complete search history.

(56) References Cited

U.S. PATENT DOCUMENTS 3,699,952 A * 10/1972 Waters .................... A46B 13/02
601/18
4,397,055 A * 8/1983 Cuchiara ............ A61C 17/3472
15/22.1
(Continued)

FOREIGN PATENT DOCUMENTS

WO    WO2009066077    5/2009

*Primary Examiner* — Justine R Yu
*Assistant Examiner* — Christopher E Miller
(74) *Attorney, Agent, or Firm* — Joel Douglas

(57) ABSTRACT

Disclosed herein is an improved eyelid care appliance and method of using such appliance for preventing and treating blepharitis and mammalian meibomian gland dysfunction caused by gland obstruction. The method and apparatus of the invention enable restoration and maintenance of eyelid hygiene and the natural flow of secretions from the meibomian glands. A preferred embodiment of the apparatus has an oscillating brush head affixed to the distal end of the eyelid care appliance. The brush head can be impregnated with topical pharmacologic or cleansing agents to better facilitate cleaning and therapeutic efficacy.

9 Claims, 13 Drawing Sheets

Related U.S. Application Data

(60) Provisional application No. 62/011,591, filed on Jun. 13, 2014, provisional application No. 61/922,791, filed on Dec. 31, 2013.

(51) Int. Cl.
| | | |
|---|---|---|
| *A61H 23/02* | (2006.01) | |
| *A61F 9/007* | (2006.01) | |
| *A61H 35/02* | (2006.01) | |
| *G09B 19/00* | (2006.01) | |
| *A46B 9/02* | (2006.01) | |
| *A46B 13/00* | (2006.01) | |
| *A46B 13/02* | (2006.01) | |

(52) U.S. Cl.
CPC .............. *A61H 2201/105* (2013.01); *A61H 2201/1215* (2013.01); *A61H 2201/1604* (2013.01); *A61H 2201/1685* (2013.01); *A61H 2201/5035* (2013.01); *A61H 2201/5043* (2013.01); *A61H 2201/5048* (2013.01); *A61H 2201/5064* (2013.01); *A61H 2201/5097* (2013.01); *A61H 2205/024* (2013.01)

(56) References Cited

U.S. PATENT DOCUMENTS

| | | | |
|---|---|---|---|
| 4,883,454 A | 11/1989 | Hamburg | |
| 5,974,615 A * | 11/1999 | Schwarz-Hartmann | A61C 17/3472 15/22.4 |
| 6,579,251 B1 * | 6/2003 | Randoll | A61H 23/0254 601/89 |
| 7,571,508 B1 * | 8/2009 | Yufa | A46B 13/02 15/144.4 |
| 8,523,928 B2 | 9/2013 | Korb et al. | |
| 8,561,241 B2 * | 10/2013 | Lim | B05B 3/1007 15/22.2 |
| 9,154,025 B2 * | 10/2015 | Schaefer | A61C 17/3436 |
| 9,226,808 B2 * | 1/2016 | Utsch | A61C 17/3436 |
| 2002/0156402 A1 * | 10/2002 | Woog | A61H 23/0236 601/46 |
| 2005/0154381 A1 * | 7/2005 | Altshuler | A61B 18/20 606/9 |
| 2005/0177139 A1 * | 8/2005 | Yamazaki | A45D 26/00 606/9 |
| 2006/0058714 A1 * | 3/2006 | Rhoades | A45D 34/04 601/73 |
| 2008/0081996 A1 * | 4/2008 | Grenon | A61B 5/411 600/443 |
| 2010/0214532 A1 * | 8/2010 | Siminou | A61B 3/14 351/206 |
| 2011/0237999 A1 * | 9/2011 | Muller | A61B 3/107 604/20 |
| 2012/0059224 A1 * | 3/2012 | Wellen | A61B 1/227 600/200 |
| 2012/0065555 A1 | 3/2012 | Smith et al. | |
| 2012/0065556 A1 * | 3/2012 | Smith | A61F 7/007 601/89 |
| 2012/0320340 A1 * | 12/2012 | Coleman, III | A61B 3/10 351/208 |
| 2013/0046367 A1 * | 2/2013 | Chen | A61B 18/08 607/113 |
| 2013/0085459 A1 * | 4/2013 | Voss | A61B 3/113 604/290 |
| 2013/0331768 A1 * | 12/2013 | Nichamin | A61P 29/00 604/22 |
| 2014/0052164 A1 | 2/2014 | Rynerson | |
| 2014/0085603 A1 * | 3/2014 | Su | A61B 3/0041 351/206 |
| 2014/0135798 A1 * | 5/2014 | David | A61H 7/005 606/131 |
| 2014/0142471 A1 * | 5/2014 | Chambon | A61B 18/203 601/18 |
| 2014/0214062 A1 | 7/2014 | Rynerson | |
| 2014/0249509 A1 * | 9/2014 | Rubinfeld | A61F 9/0008 604/521 |
| 2014/0031845 A1 | 11/2014 | Rynerson | |
| 2015/0216722 A1 * | 8/2015 | Choate | A61F 9/00772 606/162 |
| 2015/0313467 A1 * | 11/2015 | Sakai | A61B 3/0016 351/208 |
| 2015/0320590 A1 * | 11/2015 | Whitehurst | A61F 7/08 607/109 |

* cited by examiner

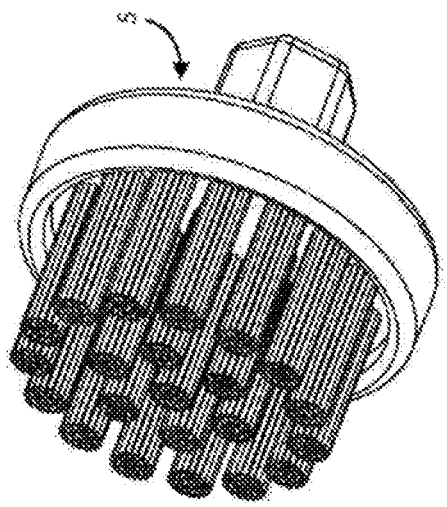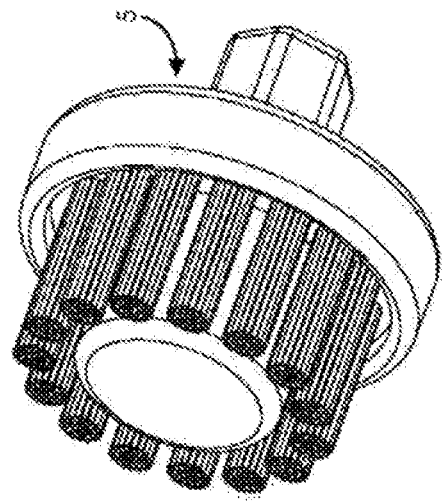
Figure 12c  Figure 13c
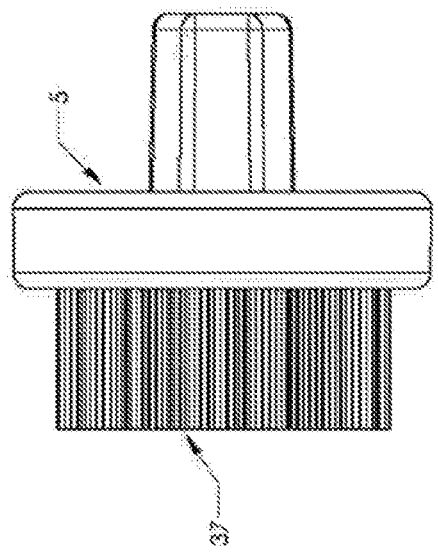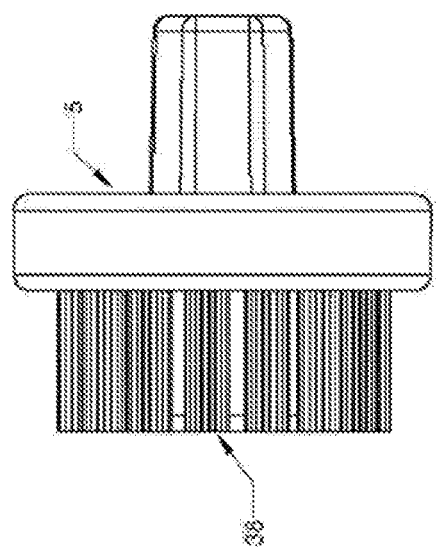
Figure 12b  Figure 13b
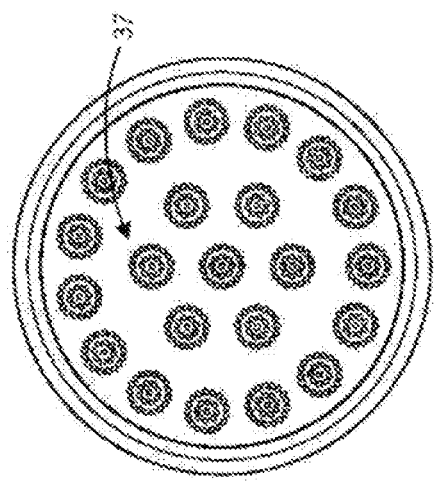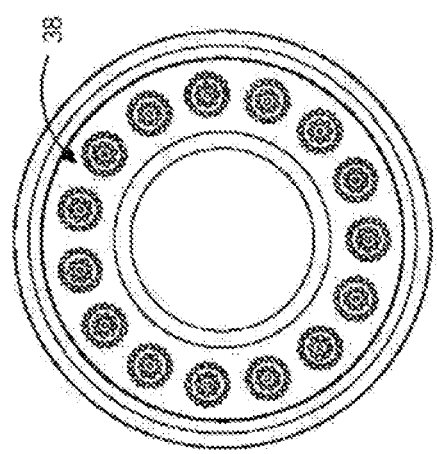
Figure 12a  Figure 13a

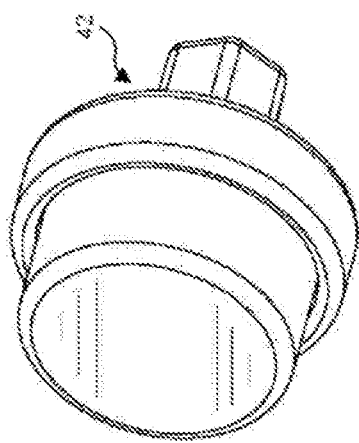
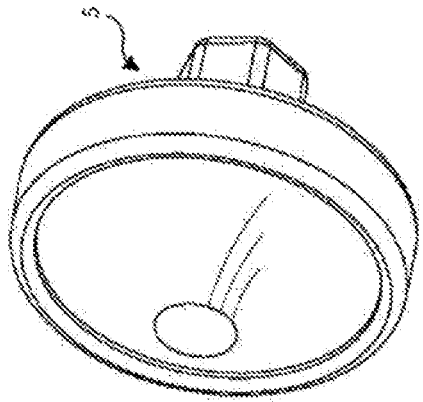
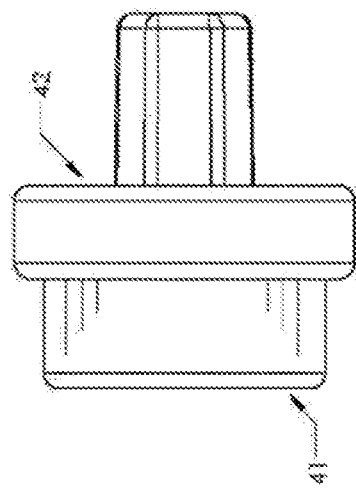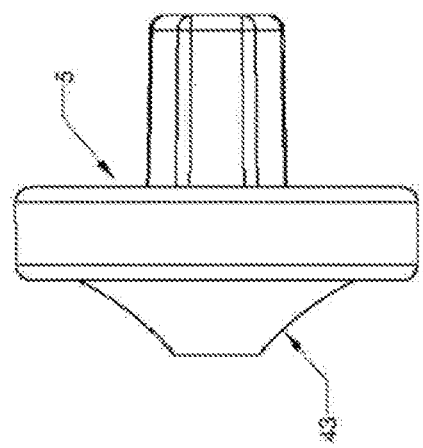
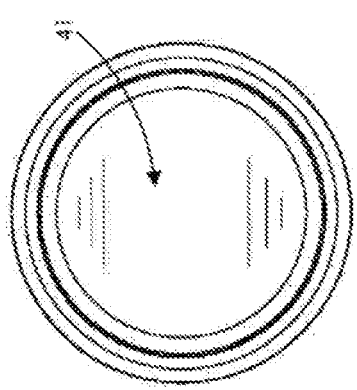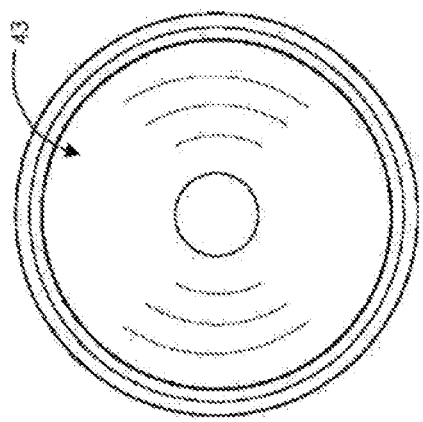
Figure 16a  Figure 16b  Figure 16c
Figure 17a  Figure 17b  Figure 17c

EYELID CARE APPLIANCE

RELATED APPLICATIONS

This application claims the benefit under 35 U.S.C. 119(e) of U.S. Provisional Application No. 61/922,791 filed 31 Dec. 2013 and U.S. Provisional Application No. 62/011,591 filed 13 Jun. 2013 and U.S. patent application Ser. No. 14/588,392 filed 31 Dec. 2014.

BACKGROUND OF THE INVENTION

Field of the Invention

This invention relates to a new and improved method and apparatus to clean debris from eyelids, to treat blepharitis, and to prevent meibomian gland obstruction, which method and apparatus permit self-administered eyelid cleaning and treatment.

Description of Related Art

"Dry eye" is the world's most common eye disease. "Dry eye" indicates the lack of quantity and/or quality of the tear film. In the human eye, the tear film covering the ocular surfaces is composed of three layers. The innermost layer in contact with the ocular surface is the mucus layer, comprised of many mucins. The middle layer, comprising the bulk of the tear film, is the aqueous (water) layer, and the outermost layer is a thin (less than 250 nm) layer ("lipid layer") comprised of many lipids. The typical upper eyelid has about 25 meibomian glands and the lower eyelid has about 20 meibomian glands. The meibomian gland orifices open onto the eyelid margin at and around the junction of the inner mucous membrane and the outer skin of the eyelids; that junction is termed the mucocutaneous junction.

The upward phase of blinking causes the upper eyelid to pull a sheet of the lipids secreted by the meibomian glands upward and over the other two layers of the tear film, thus forming a type of protective coating which limits the rate at which the underlying layers evaporate. Thus, a defective lipid layer or an incorrect quantity of such lipids can result in accelerated evaporation of the aqueous layer which, in turn, causes symptoms such as itchiness, burning, irritation, and dryness, which are collectively referred to as "dry eye". When left untreated, the consequences of dry eye can be severe, and even result in loss of vision (e.g., from desiccation of the corneal epithelium, ulceration and perforation of the cornea, or an increased incidence of infectious disease).

Dry eye states have many etiologies. A common cause of dry eye states disorder in which the glands are obstructed or occluded, usually referred to as "meibomian gland dysfunction" ("MGD"). Meibomian gland dysfunction is frequently the result of keratotic obstructions which partially or completely block the meibomian gland orifices. Such obstructions compromise the secretory functions of the individual meibomian glands. More particularly, these keratotic obstructions can comprise combinations of bacteria, sebaceous ground substance, dead cells, and/or desquamated epithelial cells.

Additional causes of the dysfunction of the lipid layer are associated with eyelid margin inflammation (e.g., anterior and posterior blepharitis, hordeolum, sty, chalazion, and rosacea). The etiological factors of many of these inflammations, include an overgrowth of bacteria (and/or parasites) and their toxic waste. These bacteria not only cause the lipid tear film to dysfunction, but they also destroy and block the very lipid-producing infrastructure by attacking the glands in the eyelid skin. Unfortunately, the particular types of bacteria and parasites that cause the inflammation/infections are common. The chance of having these on the eyelids is nearly 100%. In themselves, they are not dangerous, but it is the overgrowth and their toxic waste on the eyelid margin and the eyelashes that must be avoided. Allowing the bacteria and parasites to proliferate must be prevented, especially if one is diagnosed as a dry eye sufferer.

While the tear film operates as a singular entity and all of the layers are important, the lipid layer, which is secreted from the meibomian glands, is of particular significance as it functions to slow the evaporation of the underlying layers and to lubricate the eyelid during blinking; such slowing of evaporation and lubrication of the eyelid largely prevent "dry eye syndrome".

Thus, to summarize, the meibomian glands of mammalian (e.g., human) eyelids secrete oils that prevent evaporation of the tear film and provide lubrication to the eye and eyelids. These glands can become blocked or plugged by various mechanisms leading to so-called "dry eye syndrome". While not the only cause, meibomian gland dysfunction is a major cause of dry eye syndrome. Dry eye syndrome is characterized by a blockage of the meibomian glands, which prevents normal lipid secretions from flowing from the meibomian glands to form the lipid layer of the tear film.

Various treatment modalities have been developed to treat the dry eye condition, including drops which are intended to replicate and replace the natural tear film, and pharmaceuticals which are intended to stimulate the tear producing cells. Various heating devices are commercially available that are designed to assist in unclogging the meibomian glands by "melting" blockages of the meibomian glands. Other techniques involve manual expression of the glands and manual scrubbing of the eyelid margins.

Eye drops such as REFRESH®, SOOTHE® and SYSTANE® brand eye drops are designed to closely replicate the naturally occurring healthy tear film. However, their use and administration is merely a treatment of symptoms and not of the underlying cause. The effect of applying eye drops is short-lived. Further, the use of drops is generally for an indefinite length of time and consequently, extended use can become burdensome and costly.

Since dry eye is exacerbated by eyelid margin debris and bacterial overgrowth, daily eyelid hygiene is often prescribed by physicians and recommended by health institutions worldwide. This is for the life of the patient, because, as mentioned, dry eye is chronic, with no known cure: unless proper eyelid hygiene is instituted, dry eye syndrome will only worsen with age.

Herein lie the unsolved problems. No existing eyelid care device enables self-administered eyelid treatment using a motorized handpiece; all prior art motorized appliances are for clinical use. A second problem is the risk of patient injury during training of eyelid care professionals, and of lay persons who use a motorized eyelid care appliance for cleaning their own eyelids ("self-administered cleaning" or "SA Cleaning") or for cleaning others' eyelids ("second party cleaning" or "SP Cleaning"). The "second party" can be a pet (blepharitis is common in dogs and cats). A third problem is that all prior art eyelid care devices with motorized handpieces use unidirectional rotary tools (aka "heads") that become entangled with hair A fourth problem is that eyelid care devices with rotary tools cause many patients to flinch when the tool first contacts the eyelid margin; such flinching increases the risk of contact by the tool with the cornea, sclera, or other parts of the eye and resulting laceration or other injury. A fifth problem is a lack of instrumentation of prior art motorized eyelid care devices, which instrumentation (e.g., proximity monitoring, cleaning efficacy) and features (e.g., safety shutoff) would enable safer use of an eyelid care device as well as data collection and analysis of clinical signs and efficacy of cleaning.

People tend to wash their face, but not their eyelids. Eyelid hygiene should optimally be performed on a daily basis for maximum efficacy and optimal hygiene. Currently only manual scrubbing methods with cloths or fingers is available for daily home use, but such manual methods are like brushing one's teeth with a washcloth. Just as brushing one's teeth with a washcloth does not clean the gingival sulcus or mesio-distal aspects of teeth, an eyelid scrub, typically contacts only the anterio ciliary margin and does not dean the entire confluence of the mucosal surface of the conjunctiva and the cutaneous epithelium. Even though daily eyelid hygiene is critically important for patients with an eyelid disease, there is typically no compliance by patients for whom SA Cleaning is ordered by their ophthalmologist. Due to a lack of alternatives, "baby shampoo" and a washcloth or cotton-tipped swab is often recommended by ophthalmologists for a patient's SA Cleaning. This current "prescription" for eye hygiene has significant non-compliance issues, i.e., patients fail to perform SA Cleaning. For instance, in a "baby shampoo regimen" the baby shampoo is mixed with warm or hot water in a prescribed ratio, and the solution is then applied with non-sterile applicators such as finger tips, cotton tips, or washcloths (typically, unsanitary).

Although commercial "eyelid scrubs" are available, in several forms, such as impregnated, pre-moistened towelettes or pads, or as bottled cleansers applied to a non-sterile applicator pad or to fingertips, such eyelid scrubs do not improve patient compliance or efficacy. These rely on the individual to perform vigorous back and forth scrubbing of all four eyelid margins, which is cumbersome, time consuming, sometimes painful, and has uneven results all of which are strong disincentives to observe a an eyelid cleaning regimen.

Preventive and therapeutic interventions need to be more easily implemented at an earlier age, or stage, of dry eye syndrome development to decrease the likelihood of chronically scarred and/or dysfunctional meibomian glands. Lack of patient compliance is further evidenced by way of disproportionate commercial sales for eye care products, which shows a clear indication that people simply do not clean their eyelids: in contrast to the US current eyecare market for eye drops (excluding contact lens solutions) of $1 billion, but eyelid scrubs show less than $8 million in retail sales.

Given existing art methods and devices, it is not surprising that there is little or no compliance to eyelid hygiene by patents. Related art describes an "Eyelid and Anterior Orbit Swab" (to Hamburg, U.S. Pat. No. 4,883,454) and various eyelid cleansers, such as U.S. Pat. Nos. 8,535,736, 8,449, 928, and 8,231,912 (to Gilbard), to dean the eyelids, but these rely solely on manual back and forth motion of a device on the eyelid margin and manual application of a cleanser.

US Published Application No. 20070060988 (by Grenon) discloses an eyelid heater that "melts" plugs that block meibomian glands and expresses the melted plugs through meibomian gland openings on the eyelid margin. Unlike the instant invention, the Grenon device does nothing to actually clean the eyelid margin.

U.S. Pat. No. 8,523,928, (Korb and Grenon) describe a system for heating eyelids. This device is used to liquefy, express and evacuate ductal obstruction, not clean debris and biofilm from the lid margin. The Korb device does nothing to actually clean the eyelid margin.

Ophthalmologists presented with a particle (usually a metal particle) embedded in a patient's cornea or sclera (or with the "rust ring" left by a particle) typically use an ophthalmic burr, such as an Algerbrush (Alger Co., Inc., Lego Vista, Tex.) or Aaron Burr (Bovie Medical Corp., Purchase N.Y.) to "scrub" the particle or "rust ring" from the cornea or sclera. Ophthalmic burr devices typically have a motorized handpiece and detachable burrs (burr diameter in the 0.5 mm to 1.0 mm range). At least one eyelid cleaning device, the BlephEx® device described in US Published Patent Application Nos. 20140031845, 20140052164, and 20140214062, uses a design and unidirectional rotation virtually identical to that of ophthalmic burrs, but with a "sponge head" instead of a burr. Like ophthalmic burrs, the BlephEx device drives a head with a full rotary motion and is for use by eyecare professionals. An "eyecare professional" is a person skilled in the art of ocular hygiene, such as ophthalmologists, optometrists, nurses trained in eyecare, and technicians trained in eyecare. The BlephEx handpiece rotates a small sponge, is guided along the eyelid margin by an eyecare professional, removes scurf and debris, and exfoliates the eyelids. The key disadvantages of the Blephex® device are its "motorized swab" design, unidirectional spinning (rotating) head (as distinct from an oscillating head moving in a reciprocally arcuate path), lack of instrumentation, and lack of safety features. Using an oscillating head to clean eyelids has significant advantages over existing art eyelid cleaning devices. Oscillating devices tend to be safer than rotary devices; an oscillating head does not have the directional "kick" start-up torque) of a rotating head, so there is less chance of a user losing control of the device, e.g., the device jumping out of the user's hand. For that reason, devices with oscillating heads are easier to control than rotary devices. An oscillating eyelid care device does not induce a flinch response in the subject when the head first contacts an eyelid. An oscillating head creates less flying debris than a rotary head, making an oscillating head a better choice for work in an area where excessive flying debris might be a nuisance, such as near the eye.

The BlephEx device can only safely be used by an eyecare professional due to the ergonomics and dynamics (e.g., "motorized swab" form, flinch induction, unidirectional rotation) of the device. The stick-like design (i.e., cylindrical handpiece with long, rotating, longitudinally aligned head) of the BlephEx i device prevents the use of a BlephEx® device for SA Cleaning, i.e., for a patient to use in performing eyelid cleaning on him/herself. A device with a stick-like design must be used by a second person, typically by an eyecare professional.

In eyelid cleaning experiments in a dog model that compared the invention with (i) manual scrubbing, (ii) the Blephex® device, (iii) a heated, vibrating cup-like device similar to that described in U.S. Pat. No. 8,491,508 (to Smith), and (iv) with motorized cosmetic appliances, such as the Clarisonic Opal® (a discoid, lotion applicator that uses an oscillating, solid silicone head), the results revealed a significant decrease in eye discharge in eyes treated with the instant invention as compared to control and to the other devices. In all trials, the eyelid margins of one eye of a subject were not cleaned, and the eyelid margins of the other eye were cleaned. When compared to manual lid scrubs the instant invention removed lid discharge more quickly and thoroughly than the manual lid scrub product. The heated, vibrating, cup-like device did not clean debris from lid margins. Testing of the Blephex® device on dogs had to be discontinued because the Blephex® device induced a strong flinching response when applied to eyelid margins, and dog hair quickly became entangled in the head of the Blephex® device, which not only caused pain to the dogs but "reeled in" the Blephex® device, which caused erratic paths of the device while the head was still spinning. Dogs could not tolerate the vibration of the Clarisonic Opal® on their eyelids, and the Clarisonic Opal® with its smooth silicone head produced no detectable cleaning action. The cleaning results in the dog model showed the eyelid care appliance of the invention to be markedly superior, based on a close examination of the uncleaned eye versus the cleaned eye, and of cleaned eyes of all subjects. The same solvents and cleansers were used in all trials. The dog model trials were conducted under a research protocol which was reviewed and approved by the Institutional Animal Care and Use Committee (IACUC) at the University of Hawaii. The assistance of a licensed veterinarian was obtained. Four dogs were given one treatment per week with the eyelid care appliance over a three week period. Due to hair entanglement and flinching response, treatment using the Blephex® device was aborted in the dog model after two treatments. Treatment using the Clarisonic Opal® was aborted during the first attempt at treatment, given the strong adverse reaction of the dogs to the Clarisonic Opal® device.

Existing powered eyecare devices have heads with a constant unidirectional rotation, which requires that the operator manually change the rotational direction (e.g., from clockwise to counterclockwise) of the head and retrace the path of cleaning to ensure efficient cleaning. An oscillating head provides better removal of debris and more uniform results than devices with unidirectional head rotation, which is the reason that oscillating heads are used in powered toothbrushes. The head of the driven attachment of a commercial, off-the-shelf powered toothbrush has a "brush head" and such driven attachment is called a "brush head attachment". Clinical studies in the dental care literature have shown that powered toothbrushes with an oscillating brush head are significantly better in reducing plaque and gingivitis compared to a manual toothbrush and brushing technique, and also compared to powered rotary toothbrushes. Just as the oscillatory movement of a powered toothbrush brush head ensures better cleaning than manual scrubbing, because a brush head typically oscillates at about 7,000 to 9,000 strokes/minute, the oscillatory movement of a powered handpiece coupled to an eyelid care module ensures better cleaning than manual scrubbing of the eyelids. The following three publications report the comparative advantages of powered oscillating head, toothbrushes.

A comparative study of plaque removing efficiency using' rotary electric and manual toothbrushes.
Swed Dent J. 1991; 15:229-234.
Cochrane Database Syst Rev. 2005; 18(2):CD002281
J Am Dent Assoc. 2003 September, 134(9):1240-4.
Manual versus powered toothbrushes: the Cochrane review.
Niederman R; ADA Council on Scientific Affairs ADA Division of Science; Journal of the American Dental Association,
Source: DSIVI-Forsyth Center for Evidence-Based Dentistry, The Forsyth Institute, Boston, Mass. 02115, USA. miederman@forsyth.org
CONCLUSIONS: Powered toothbrushes with a rotation-oscillation action achieve a significant, but modest, reduction in plaque and, gingivitis compared with manual toothbrushes.

National Institutes of Health
CochraneDatabase Syst Rev. 2005 Apr. 8; (2):CD002281.
Manual versus powered toothbrushing for oral health.
Robinson P G, Deacon S A, Deery C, Heanue M, Walmsley A D, Orthington H V, Glenny A M, Shaw W C.
Source: Department of Dental Public Health, School of Clinical Dentistry, University of Sheffield, Claremont Crescent, Sheffield, UK. peter.g.robinson@sheffield.ac.uk
CONCLUSIONS: Powered toothbrushes with a rotation oscillation action reduce plaque and gingivitis more than manual tooth brushing.
Powered/electric toothbrushes compared to manual toothbrushes for maintaining oral health—Cochrane Report June 2014.
Yaacob M, Worthington H V, Deacon S A, Deery C, Walmsley A, Robinson P G, Glenny A. This article reviews 56 studies published from 1964 to 2011 in which 5068 participants were randomised to receive either a powered toothbrush or a manual toothbrush. Majority of the studies included adults, and over 50% of the studies used a type of powered toothbrush that had an oscillation mode of action (where the brush head rotates in one direction and then the other, aka reciprocally arcuate).
CONCLUSIONS: The evidence produced shows benefits in using a powered toothbrush when compared with a manual toothbrush. There was an 11% reduction in plaque at one to three months of use, and a 21% reduction in plaque when assessed after three months of use. For gingivitis, there was a 6% reduction at one to three months of use and an 11% reduction when assessed after three months of use.

One advantage of oscillating brush head, powered toothbrushes in general is their ability to remove a greater amount of plaque in a given period of time than manual brushes. One study (Preber H, Swed. Dent. J. 1991; 15:229-234) found that 75% of dental biofilm was removed in 15 seconds with an oscillating powered toothbrush; the same amount of plaque removal required twice as long with a manual brush. The results of more thorough cleaning process with oscillating powered toothbrushes can be extrapolated to eyelid hygiene using an oscillating powered device. However, powered toothbrushes cannot be easily adapted to eyelid care, given the large size of the handpiece, brush head attachment, and brush head, the stiff bristles on toothbrush brush heads (which would lacerate the eyelid margin, cornea, and sclera if used to clean eyelid margins), and the expense of disposable "necks" (the "neck" is the detachable distal portion of a powered toothbrush that terminates in a non-removable brush head, which means the entire neck must be discarded when the brush head wears, rather that disposal of only the brush head). Because powered toothbrush necks are not easily removed and are used for months before replacement, the brush heads become unsanitary. For sanitary eyelid care, the head of a device must be easily replaceable and inexpensive, or durable and autoclavable.

There is need for an eyelid care appliance that enables SA Cleaning, reduces risk of patient injury during training of eyelid care professionals, reduces risk of patient injury during SA Cleaning and SP Cleaning, provides an oscillating head, provides instrumentation and safety features that improve efficacy of eyelid care, provides an inexpensive and easily replaceable head (and alternatively, a durable and autoclavable head) and ideally provides an adjustable head angle and optionally provides control over oscillation frequency and angular sweep.

The eyelid care appliance described and claimed herein solves the proceeding problems by providing, in a preferred embodiment, an oscillating, detachable sponge head, adjustable head angle, an ergonomic powered handpiece, sensors and other controls and instrumentation (such as, controls, indicators, displays, video, and/or data transmission), and auxiliary functions (cleanser, solvent, and medicament dispensing, gas and liquid dispensing, heating, and suction) that improve professional eyelid care, SA Cleaning, and SP Cleaning.

SUMMARY OF THE INVENTION

The apparatus of a preferred embodiment of the invention comprises a power supply (e.g., battery), motor, detachable head, drive system that causes oscillation of the head, controls, instrumentation, and a housing. "Distal" means herein toward the end of the eyelid care appliance on which the head is mounted. "Proximal" means herein toward the end of the eyelid care appliance in which the power supply and motor are mounted.

A "spongehead" is preferred for eyelid care, but other materials and configurations of heads can be used in the invention, particularly for treating epidermal areas other than eyelid margins. "Spongehead" means a synthetic sponge adhered to a "sponge mount". The sponge mount mates with a "head receiver" that is connected to and driven by a drive system so that the spongehead mated with the head receiver oscillates when the motor is powered on. A spongehead may be configured in a wide range of embodiments, some of which embodiments include various types of bristles, adjustable bristles, combinations of bristles and sponge, and other materials of varying topologies and degrees of abrasiveness.

A preferred embodiment of the eyelid care appliance is an "integral" eyelid care appliance comprising a power supply, motor, drive system that transmits motive force from the motor to, oscillate a head receiver, motor controls, a proximity system, and proximity annunciator contained in a housing, wherein a spongehead is detachably mated with the head receiver and protrudes from the housing and oscillates when the motor is powered on. A drive module (defined below) and an eyelid care module (defined below) are the principal elements contained in the housing. An alternate "two-piece" embodiment comprises a detachable neck that mates with a handpiece; the handpiece comprises the power supply, motor, and part of the drive system; the detachable neck comprises the head and remainder of the drive system. In a two-piece embodiment, the components of the eyelid care appliance can be distributed in whole or in part between the handpiece and the detachable neck, depending upon the component and configuration involved. As used herein, "handpiece" means the proximal portion of a two-piece embodiment of the invention, which proximal portion is gripped by a user.

An alternate "two-piece" embodiment of the eyelid, care appliance comprises a handpiece and a detachable neck, a power supply, motor, proximity annunciator, and motor control being contained in the handpiece, a head receiver being contained in the detachable neck and connected to the motor through a drive system with portions of the drive system distributed in the detachable neck and in the handpiece and with a coupler at the interface of the handpiece and detachable neck, which drive system transmits motive force from the motor to oscillate the head receiver, wherein a spongehead is detachably mated with the head receiver, protrudes from the detachable neck, and oscillates when the motor is powered on, and portions of a proximity system are distributed in the detachable neck and in the housing.

In the embodiments of the invention, the power supply (typically a replaceable and/or rechargeable battery) powers a DC motor, and when the motor is powered on, the motor (and drive translator, if the motor outputs unidirectional rotary motion, which motion is translated to oscillating motion) causes the oscillation of a driveshaft (or equivalent means of transmitting motive force, e.g., in a two-piece embodiment, an electric motor in a handpiece with magnetic or mechanical coupling to a detachable neck). The oscillating driveshaft causes the head receiver to oscillate, which causes the spongehead mounted in the head receiver to oscillate. The eyelid care appliance is typically battery powered, but can be powered by a power supply connected to an electrical outlet.

To use the eyelid care appliance claimed herein, a user grips the proximal portion of the appliance, powers on the appliance, and applies the oscillating head on the distal end of the appliance, together with a solvent or cleanser, to the eyelid margin to scrub the eyelid margin. In a preferred embodiment for SA Cleaning and SP Cleaning, the eyelid care appliance comprises a drive module, drive controls and annunciator, eyelid care module with adjustable head angle, proximity sensor, proximity controls and annunciator, and related data channels. A preferred configuration of proximity sensor and annunciator is a video camera, a Bluetooth or similar near field communication channel (Bluetooth, ANT+, WiFi, or other near field communications channel are collectively called, "NFC")), and a smartphone or tablet computer with near field communications capability and display (collectively, "smart device") that is paired with the eyelid care appliance: the video image from the eyelid care appliance is transmitted through the communication channel and displayed on the smart device. A user of the eyelid care appliance essentially "flies" the head onto the eyelid margin and moves the head along the margin. By focusing on the display, the user becomes immersed in control of the head rather than fearful of poking himself or herself in the eye. The proximity system can evaluate or score user performance as if the use of the eyelid care appliance were a video game.

BRIEF DESCRIPTION OF THE DRAWINGS

FIG. 12a: Bristle Head Front View FIG. 12b: Bristle Head Side View FIG. 12c: Bristle Head Isometric View FIG. 13a: Bristle Spongehead Front View FIG. 13b: Bristle Spongehead Side View FIG. 13c: Bristle Spongehead Isometric View FIG. 16a: Small, Higher Chamfer Spongehead Front View FIG. 16b: Small, Higher Chamfer Spongehead Side View FIG. 16c: Reduced Diameter Spongehead Isometric View FIG. 17a: Caldera Spongehead Front View FIG. 17b: Caldera Spongehead Side View FIG. 17c: Caldera Spongehead Isometric View

DRAWING CALLOUTS

Figure 1D:
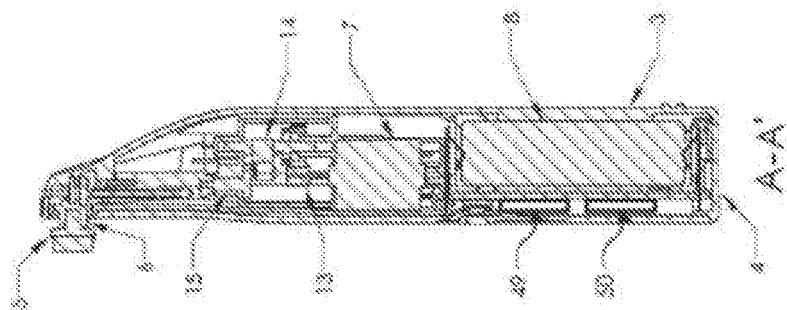
FIG. 1d: Eyelid Care Appliance, Integral Version Cross-section View
Figure 1C:
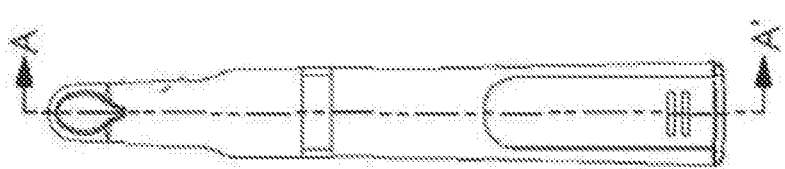
FIG. 1c: Eyelid Care Appliance Integral Version, Rear View
Figure 1B:
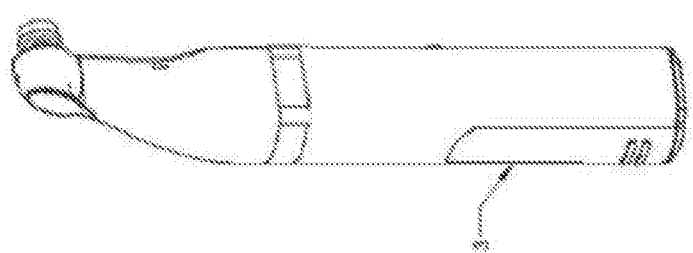
FIG. 1b: Eyelid Care Appliance, IntegralVersion, Rear Isometric View
Figure 1A:
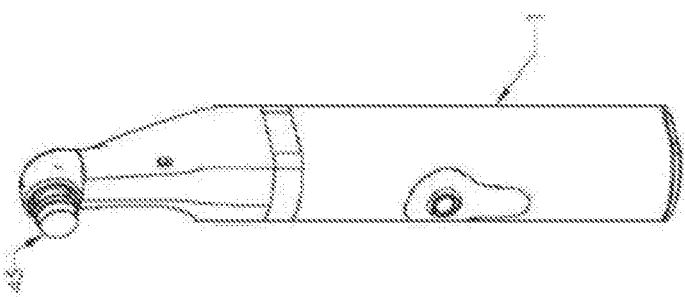
FIG. 1a: Eyelid Care Appliance, Integral Version, Front IsometricView

1: Main Housing
2: Spongehead
3: Battery Cover
4: Housing Cap
5: Sponge Mount
6: Head Receiver
7: DC Motor
8: AA, Lithium Ion 14450, or Equivalently Sized Battery
9: Battery Clip
10: Suction Pump Outlet
11: Printed Circuit Board
12: Motor Housing
13: Pinon Gear
14: Spur Gear Linkage
15: Keyed Shaft
16: Drive Housing
17: Receiver Linkage
18: Linkage Tee with Spring
19: Light Pipe and Light Ring
20: Housing Pin
21: Linkage Pin
22: Carrier Pin
23: Battery Housing
24: Power Button Over-Molding
25: Spongehead Sensors
26: LCD Display
27: LED Control
28: Suction Nozzle
29: Liquid/Gas Nozzle
30: Liquid/Gas Tubing
31: Liquid/Gas Reservoir
32: Liquid/Gas Tubing
33: Liquid/Gas Reservoir
34: Concave Spongehead
35: Pointed Spongehead
36: Convex Spongehead
37: Bristle Head
38: Bristle Spongehead
39: Concave Bristle Head
40: Convex Bristle Spongehead
41: Small, Higher Chamfer Spongehead
42: Small, Higher Chamfer Sponge Mount
43: Conical Spongehead
44: Video Camera Lens
45: Cylindrical Sponge
46: Drive System Adjustment Holes
47: Adjustable Head

DETAILED DESCRIPTION OF PREFERRED EMBODIMENTS

The present invention, the eyelid care appliance, is directed to novel devices and methods effective for restoring and maintaining good eyelid hygiene, e.g., both prophylaxis and therapeutic treatment. The methods and devices disclosed herein include those for SA Cleaning and SP Cleaning, which enable better patient compliance with prescribed eyelid cleaning regimens, esp., daily prophylaxis. The incidence of blepharitis increases as a function of age. If a person's neurological deterioration prevents them from performing SA Cleaning, a lay care-giver can perform SP Cleaning of such person's eyelids using the eyelid care appliance. These methods involve the easy and safe mechanical cleaning of an eyelid by eyecare professionals in clinical settings and by lay individuals in any location in which manipulation of the individual's eyelids or the eyelids of a second party is safe. "Second party" includes animals, especially household pets, horses, and farm animals. The present invention provides improved cleaning of the eyelid margins and meibomian gland orifices, and enables a patient to clean his or her eyelids without assistance. The invention solves the technical problems of improved eyelid cleaning and training in eyelid cleaning, esp., the technical problems in SA Cleaning and SP Cleaning.

"Head" means a spongehead unless otherwise denoted as a brush head, combination sponge and bristle head, or head made with materials other than sponge and bristles. The motive action of the driving means is transmitted through from the motor through the drive system to the head receiver. The eyelid care appliance is always used with a cleanser and/or lubricant that is applied to the sponge of the spongehead and/or directly to the eyelids being cleaned. In addition to cleanser and/or lubricants, medicaments can be applied to the spongehead and/or directly to the eyelids being cleaned. When a user turns on an eyelid care appliance, and applies the oscillating spongehead to an eyelid, oscillation of the spongehead cleans the eyelid margins and meibomian gland orifices of cellular and sebaceous debris. Such cleaning prevents, for an ensuing period, gland obstruction and promotes health of the glands in the eyelid. The oscillation frequency and angular sweep can optionally be user-selected and implement via printed circuit board 11 control of motor 7. Oscillation frequency of the head is nominally 7,000 to 9,000 strokes/minute and angular sweep of the head is nominally 70 degrees (i.e., the head travels 70 degrees forward followed by 70 degrees backwards). Higher frequency pulsation (nominally 20,000 to 40,000 pulses/min.) can optionally be generated by the motor 11 and fed to the head receiver 6.

A basic embodiment of the invention comprises a power supply (e.g., battery), drive module that causes oscillation of a head receiver, detachable spongehead mounted in the head receiver, drive control, and a housing that contains the preceding elements. The housing has a proximal portion, preferably ergonomic, that is easily gripped by hand. The proximal portion of the housing in this embodiment also contains drive control (at least on/off, and optionally status LED(s), oscillation frequency, oscillation sweep angle, and timer). A status LED can indicate simply power on (if lit), or one or more LEDs can additionally indicate battery charge level, spongehead oscillation frequency, and other operational states.

Figure 18B:
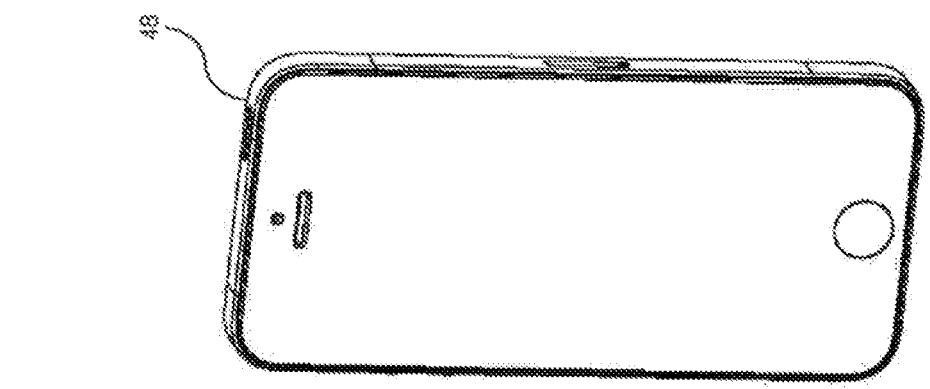
FIG. 18b: Eyelid Care Appliance with Video Proximity System and Near Field Communication Channel to Smart Device
Figure 18B:
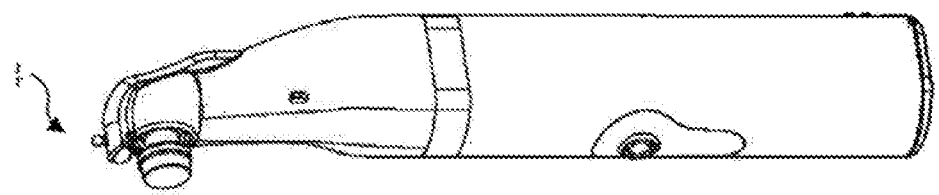
Figure 18A:
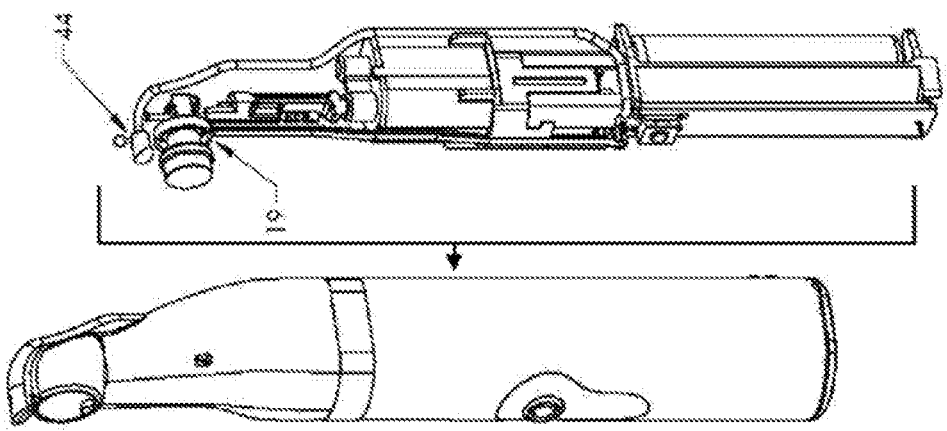
FIG. 18a: Eyelid Care Appliance with Video Proximity System
Figure 18C:
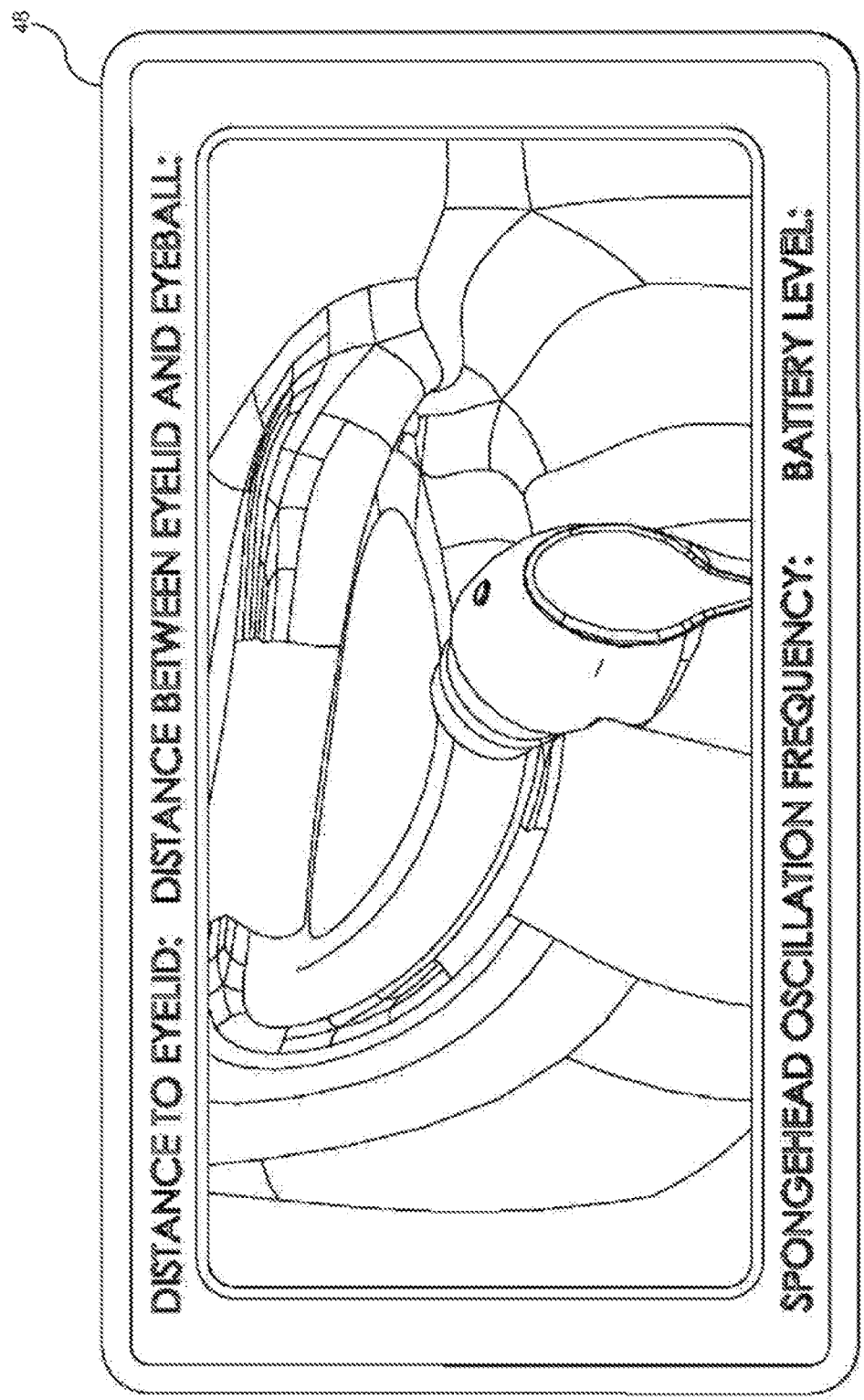
FIG. 18c: Smart Device Display Showing Video from Eyelid Care Appliance Provided by Video Proximity System via Near Field Communication Channel

A preferred embodiment of the invention comprises a power supply (e.g., battery), drive module that causes oscillation of a head receiver, detachable spongehead mounted in the head receiver, drive control and annunciator, proximity system, and a housing that contains the preceding elements. The housing has a proximal portion, preferably ergonomic, that is easily gripped by hand. The proximal portion of the housing in this embodiment also contains drive control (described above) and proximity control and annunciator. The details of the proximity system, control, and annunciator depend upon the configuration of the proximity system. In a video proximity system, the control is at least on/off (and optionally typical video controls, such as manual or auto iris, and gain) and the annunciator is preferably a mobile display linked to the video camera by NFC. In this embodiment, proximity system control is preferably performed through one or more software applications ("smart apps") running on the smart device and would enable recording video of the eyelid cleaning in, the memory of the smart device or of the eyelid care appliance. Proximity system settings performed by smart apps or by applications running on the printed circuit board 11 can include the generation of audible tones that reflect distance between the spongehead and the closest surface and optionally the second closest surface to the spongehead (typically the eyelid margin is closest and the cornea or sclera is second closest surface), colors or icons on the smart device display that indicate distance, or the generation of a glideslope display on the smart device that guides a user in landing the spongehead on an eyelid margin. Preferably, one or more lights (e.g., LEDs) on the housing project light in front of the spongehead in video-equipped embodiments of the invention. The output of the proximity system software can include the distance between spongehead and eyelid, the distance between eyelid and eyeball, the battery level, the spongehead oscillation frequency, and other data to assist the user; such output can be displayed on the smart device, as shown in FIG. 18c. The proximity system can evaluate or score user performance as if the use of the eyelid care appliance were a video game. This embodiment is called the "simple proximity embodiment" of the invention. Alternative embodiments include a video display (typically, an LCD) mounted on or integral with the eyelid care appliance, projected video, or a video goggle. A video-based proximity system also provides magnification of the treated area and documentation of the progress, and thus makes it easier to learn to use the eyelid care appliance and to visually confirm cleanliness of treatment area.

A "spongehead" is preferred for eyelid care, but other materials and configurations of heads can be used in the invention, particularly for treating areas other than eyelid margins. "Spongehead" means a synthetic sponge in a disc, cylindrical, globular, and other shape that is adhered to a "sponge mount". A spongehead of the invention comprises (i) a solid sponge mount with a male or female portion (preferably a male mating portion, such as a post) that mates with a "head receiver" (preferably with a female mating portion, such as a socket) and (ii) a sponge (or other material adapted for cleaning eyelid margins or other areas) selected for use for cleaning a target surface, such as eyelid margins. Key selection factors for the sponge material are; surface topology, elasticity, shape memory, degree of smoothness, level of porosity, and hydrophilic nature of the sponge. Material selection determines whether the spongehead is inexpensive, or durable and autoclavable. A sponge mount mates with a head receiver that is connected to and driven by the drive system so that the spongehead mated with the head receiver oscillates when the motor is powered on. Friction between the post and socket in the sponge mount/head receiver interface are typically more than adequate to keep the spongehead firmly affixed to the head receiver, but still removable for replacement of the spongehead. Alternatively, a weak adhesive can be applied, or a physical detent used in the plug and socket, to more firmly retain the spongehead in the head receiver, yet permit removal of the spongehead without tools. The sponge mount and head receiver are typically made of a plastic selected to withstand rapid oscillation and devoid of small cavities that can be colonized by bacteria. A post can have any shape that prevents rotation or slippage of the sponge mount when the sponge mount is mated with the head receiver. The post shape is preferably a polygonal shape, such as a hexagon, triangle, rectangle, or star-shape.

The sponge material, porosity, shape, and other parameters are selected based on treatment objectives, e.g., maintaining eyelid health, treating eyelid conditions and diseases, dermabrasion, polishing, etc. Sponge materials may be low-density polyether, polyvinyl alcohol ("PVA", which is highly absorbent), polyester (almost as absorbent as PVA, but more durable and has larger pores), and other polymers. A spongehead can have various surface textures, topologies, porosities, permeabililties, dimensions, inlet (e.g., suction) channels, and outlet (e.g., dispensing) channels. The sponges of spongeheads can be pre-impregnated with topical pharmacologic or cleansing agents to better facilitate application and efficacy of said agents. Alternatively, topical agents can be applied to the sponge before applying the head to an eyelid, or can be applied using a reservoir-equipped embodiment of the invention.

The sponge used in the invention is preferably sterile and can be easily replaced. The spongehead is sterilized and distributed to users in packaging that maintain sterility. Sterility is desired since a spongehead is used to clean eyelids and in close proximity to the cornea and other exposed parts of the eye, and in other embodiments is used in debridement and wound treatment. A spongehead can be easily replaced by pulling it off the head receiver. Periodic replacement of a disposable spongehead is typically daily in a home use setting (i.e., for SA Cleaning), or for each patient in a clinical setting.

Alternative embodiments of the instant invention comprise one or more of the following elements: (i) illumination source(s) with on off and optionally with light intensity control, (ii) one or more refillable reservoirs, pumps, and outlet channels for solvent, cleanser, medicament, and other liquids, powders, and gases (the gases may be heated, cooled, or room temperature and may be used to create an aerosol from a liquid or powder), (iii) means of metering and application of liquids, powders (and other solids), and gases, (iv) a suction pump that creates suction in or near the spongehead to remove debris, cleanser, and other matter from a surface being cleaned or treated, (v) sensors and optionally processors to assay the distance from head to target area, materials in target area, and/or materials in suction wastestream, (vi) indicators (visual and aural) and displays, (vii) video camera, and (viii) data communication channels (wired and/or wireless). The hardware and software used to perform an assay may be located in the handpiece or located remotely and linked with the eyelid care appliance by NFC. A head can also comprise bristles, typically very small diameter bristles, alone on in combination a sponge. In some spongehead embodiments, the bristles terminate very close to the surface of a spongehead. Refilling a reservoir is performed by connecting a liquid, gas, or powder source to an inlet connector on the housing in communication with the reservoir. Alternatively, a reservoir can be removed from the housing for refilling. An eyelid care appliance can comprise one or more reservoirs, reservoir inlet connectors, pumps, output tubing, and nozzles for dispensing solvent, cleanser, medicament, and other liquids, powders, and gases. Configurations with two reservoirs and associated pumps and tubing can be, filled with agents that create heat when combined; when such agents are dispensed and combine on the eyelid surface, the eyelid surface is heated, thereby helping to "melt" blockages of meibomian glands posterior to the anterior surface or an eyelid.

A preferred embodiment further comprises one or more reservoirs, reservoir inlet connectors, pumps, output tubing, and nozzles for dispensing liquids selected from the group comprising cleaning agents, Betadine, antiseptics, antimicrobials, anti-inflammatories, anesthetics, saline solution, water, solvents, taggants, stains, pharmaceuticals, nutriceuticals, and monoclonal antibodies. Another preferred embodiment further comprises one or more reservoirs, reservoir inlet connectors, housing inlets, pumps, output tubing, and nozzles for dispensing gases, wherein optionally the gases are heated or cooled by a thermal device in the output tubing and can optionally be used to create an aerosol from a liquid or powder sourced from a different reservoir, and can optionally be used to create an aerosol from a liquid or powder in such different reservoir. The gas can be ambient air fed to the pump from an inlet in the housing rather than from a reservoir.

The preferred embodiment is an "integral" eyelid care appliance in which all elements of a given configuration are contained in a single housing; a drive module (defined below) and an eyelid care module (defined below) are the principal elements contained in the housing. A preferred embodiment comprises a power supply, motor, drive system that transmits motive force from the motor to oscillate a head receiver, motor controls, a proximity system, and proximity annunciator contained in a housing, wherein a spongehead is detachably mated with the head receiver and protrudes from the housing and oscillates when the motor is powered on. An alternate "two-piece" embodiment comprises a handpiece and a detachable neck, a power supply, motor, proximity annunciator, and motor control being contained in the handpiece, a head receiver being contained in the detachable neck and connected to the motor through a drive system with portions of the drive system distributed in the detachable neck and in the handpiece and with a coupler at the interface of the handpiece and detachable neck, which drive system transmits motive force from the motor to oscillate the head receiver, wherein a spongehead is detachably mated with the head receiver, protrudes from the detachable neck, and oscillates when the motor is powered on. In a two-piece embodiment, each of the components recited in items (i) to (viii) above can be distributed in whole or in part between the handpiece and the detachable neck, depending upon the component and configuration involved. In two-piece embodiments of the invention, the detachable neck comprises an eyelid care module; the neck is detachably mated with a handpiece containing a drive module and the interface between the detachable neck and the handpiece includes a drive system interface (e.g., a mechanical coupling such as a male shaft mating with a female receiver, wherein the shaft and receiver have mating geometries, such as a D-shape, triangle shape, star shape, etc., or a magnetic coupling).

In all embodiments of the invention, a power supply (typically a replaceable and/or rechargeable battery) powers a DC motor, and when the motor is powered on, the motor (and drive translator, if the motor outputs unidirectional rotary motion) causes the oscillation of a driveshaft (or equivalent means of transmitting motive force, e.g., in a two-piece embodiment, an electric motor with magnetic or mechanical coupling to a detachable neck). The oscillating driveshaft causes the head receiver to oscillate, which causes the spongehead mounted in the head receiver to oscillate. The eyelid care appliance is typically battery powered, but can be powered by a power supply connected to an electrical outlet.

A "drive module" comprises a power supply, motor, on/off control, drive shaft, and related transmission elements. If the motor outputs unidirectional rotary motion, such unidirectional rotary motion is translated so that the driveshaft causes the head to oscillate. The combination of the motor, driveshaft, and related transmission elements (such as a drive translator) is called a "drive system". A well-known drive translator has a motor-driven driveshaft with pinion gear driving a geared disc or cam; an eccentric follower link on the geared disc or cam causes a shaft linked to the geared disc or cam to oscillate. The drive system couples the motive force of the motor to the head.

An "eyelid care module" comprises at least a spongehead, head receiver, and associated drive system. Integral and two-piece embodiments of the invention can be configured to provide the same functionality; functionality of two-piece embodiments may be limited by the functionality of the handpiece, however. For instance, a detachable neck (containing an eyelid care module) that mates with a generic powered handpiece, an electric toothbrush handpiece, would have to have additional functionality configured in the detachable neck.

As shown in FIGS. 1a to 1d, and 2a to 2c, a basic embodiment of the invention comprises a drive module and an eyelid care module in a single, "integral" housing 1. A spongehead 2 comprising a sponge 45 and a sponge mount 5 is mounted on the distal end of the appliance. A sponge 45 of a given geometry (described below) is permanently adhered to a sponge mount 5.

Figure 19:
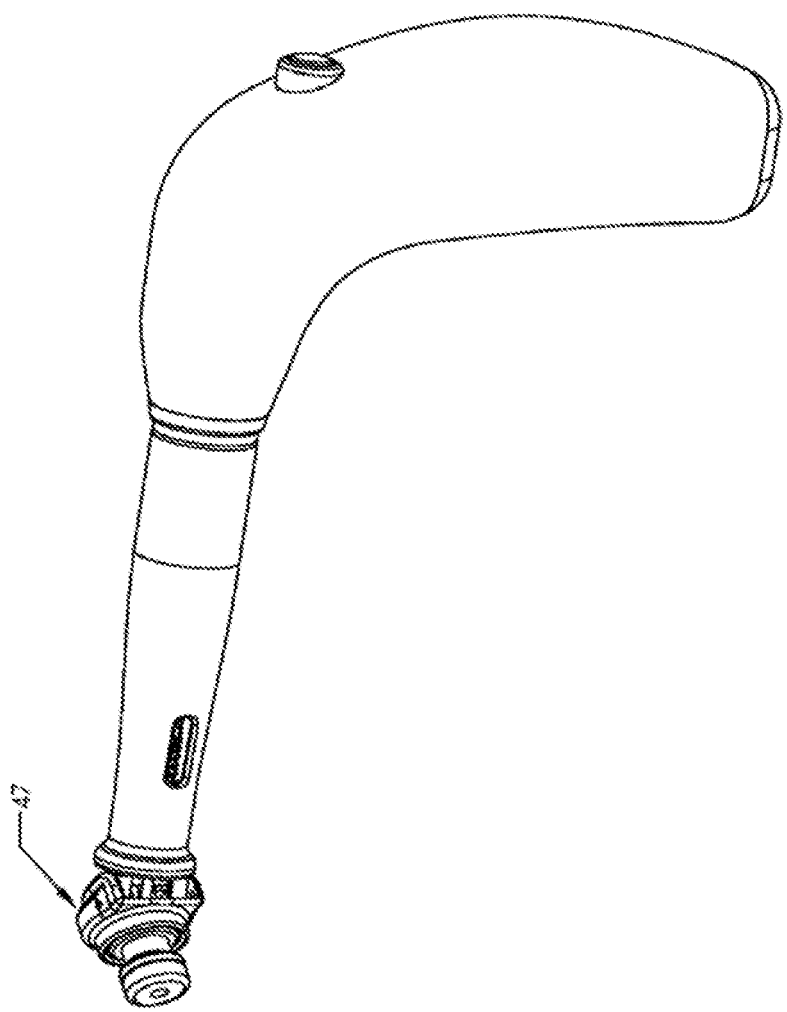
FIG. 19: Eyelid Care Appliance with Adjustable Head Angle and Pistol Grip

In embodiments in which the head angle (the angle between the axis of oscillation of the spongehead and the longitudinal axis of the housing 1 is non-adjustable, the head angle is fixed between zero and 90 degrees. In embodiments in which the head angle is adjustable (see FIG. 19), the head receiver pivots in a frame that either has detents at given head angles (e.g., 30 degrees, 45 degrees, 60 degrees, etc.) or has a locking mechanism that holds the head at a user selectable head angle. The spongehead can also be locked in place at each detent position. The preferable head angle is typically in the range from 20 degrees to 80 degrees, and preferably in the range of 45 to 65 degrees. The primary factor in selecting the head angle is to facilitate SA Cleaning and to accommodate user comfort in holding and manipulating the eyelid care appliance. Both integral and two-piece embodiments of the invention can have a head receiver with adjustable head angle ("adjustable head receiver"). Embodiments of the eyelid care attachment with adjustable head receivers can use a ball joint, U-joint, or geared joint as part of the drive system. An extension shaft with compatible male and female ends can be inserted between the sponge mount and the head receiver, just, like using an extension shaft in a socket wrench set.

An alternative configuration of the head receiver and drive system places an adjustable head receiver at the distal tip of the eyelid care appliance, and the head angle can be adjusted through a range up to 180 degrees (i.e., +90 degree head angle to −90 degree head angle) and fixed at a given head angle through detents and/or locking mechanism. Such expanded range of head angles avoids the need to invert the eyelid care appliance when cleaning the upper eyelid margins, and also keeps the on/off button in the same location within the user's grip. An adjustable head receiver embodiment of the eyelid care appliance facilitates different angulations of treatment and therapy. A preferred adjustable head receiver embodiment has detents in the head receiver at specific angulations, e.g., 45, 90, 135 and 180 degrees of head angle. The spongehead can be locked in place at each detent position. A second preferred adjustable head receiver embodiment can be locked in place, e.g., by a clamping means, at any angulation with the range of head angulation.

As shown in FIG. 1d, a battery 8 is fitted in a battery compartment in the proximal end of the main housing 1. Battery access is through a battery door 3. Housing cap 4 seals the proximal end. A DC motor 7 with a pinion gear 13 on its output shaft drives a spur gear linkage 14 that converts rotary motion of the pinion gear 13 to oscillating (reciprocally arcuate) motion and drives a keyed shaft 15. The keyed shaft 15 causes the head receiver 6 to oscillate. The sponge mount 5 with affixed sponge fits firmly (either by friction or by detent) into a head receiver 6, and oscillates in a fixed relationship to the head receiver 6. If a rechargeable battery is used as the power source in the handpiece, a means of recharging (e.g., inductive, or conductive terminals) the battery can be incorporated into a stand or holder for the device of the invention; alternatively, the battery can be remove through battery cover 3 for recharging in a charging dock.

In a preferred embodiment for SA Cleaning and SP Cleaning, the eyelid care appliance comprises a drive module, drive controls and annunciator, eyelid care module with adjustable head angle, proximity sensor, proximity controls and annunciator, and related data channels. The proximity sensor determines or depicts the distance between the surface of the head and the eyelid margin. The proximity annunciator can be a light or a light array, a display, a generated voice, or tactile. A preferred configuration, as shown in FIGS. 18a, 18b, and 18c, of proximity sensor and annunciator is a video camera 44 linked to a smartphone or tablet computer with display (collectively, "smart device") that is paired with the eyelid care appliance by NFC; the video image from the eyelid care appliance is transmitted through NFC and displayed on the smart device. The video camera 44 is preferably on a small gooseneck that can slide within a yoke, or be detached from the yoke to change the point of view of the video camera. As shown in FIG. 18c, a user of the eyelid care appliance with video proximity system "lands" the spongehead on the eyelid margin and moves the spongehead along the eyelid margin during cleaning of a margin. This preferred embodiment comprises a power supply, motor, drive system that transmits motive force from the motor to oscillate a head receiver, motor controls a proximity system, and proximity annunciator contained in a housing, wherein a spongehead is detachably mated with the head receiver and protrudes from the housing and oscillates when the motor is powered on, wherein the proximity system is a video camera with lens mounted near the spongehead and in near field communication with a smart device, and wherein the video output from the video camera is displayed on the smart device. By focusing on the smart device display linked to the eyelid care appliance by a near field communication channel, the user becomes immersed in control of the spongehead rather than fearful of poking himself or herself in the eye. The proximity system can evaluate or score user performance as if the use of the eyelid care appliance were a video game.

Figure 2C:
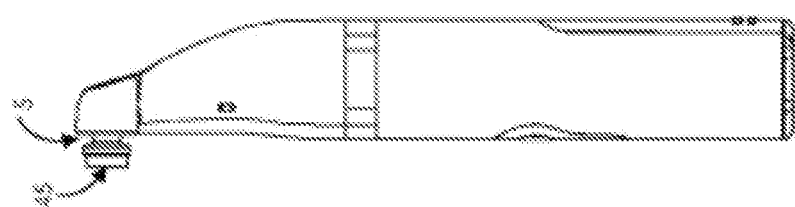
FIG. 2c: Eyelid Care Appliance, Integral Version, Side View
Figure 2B:
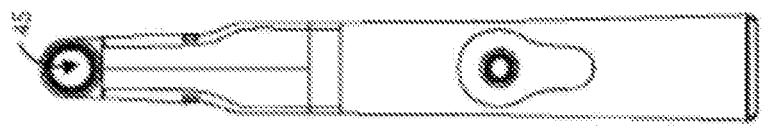
FIG. 2b: Eyelid Care Appliance, Integral Version, Front View
Figure 2A:
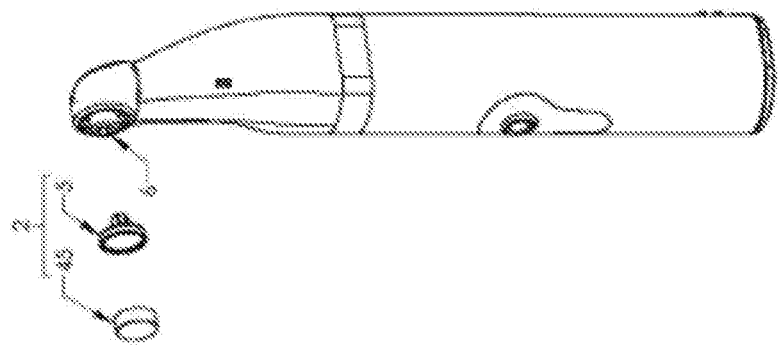
FIG. 2a: Eyelid Care Appliance, Integral Version, Exploded View with Spongehead Detached from Receiver
Figure 3:
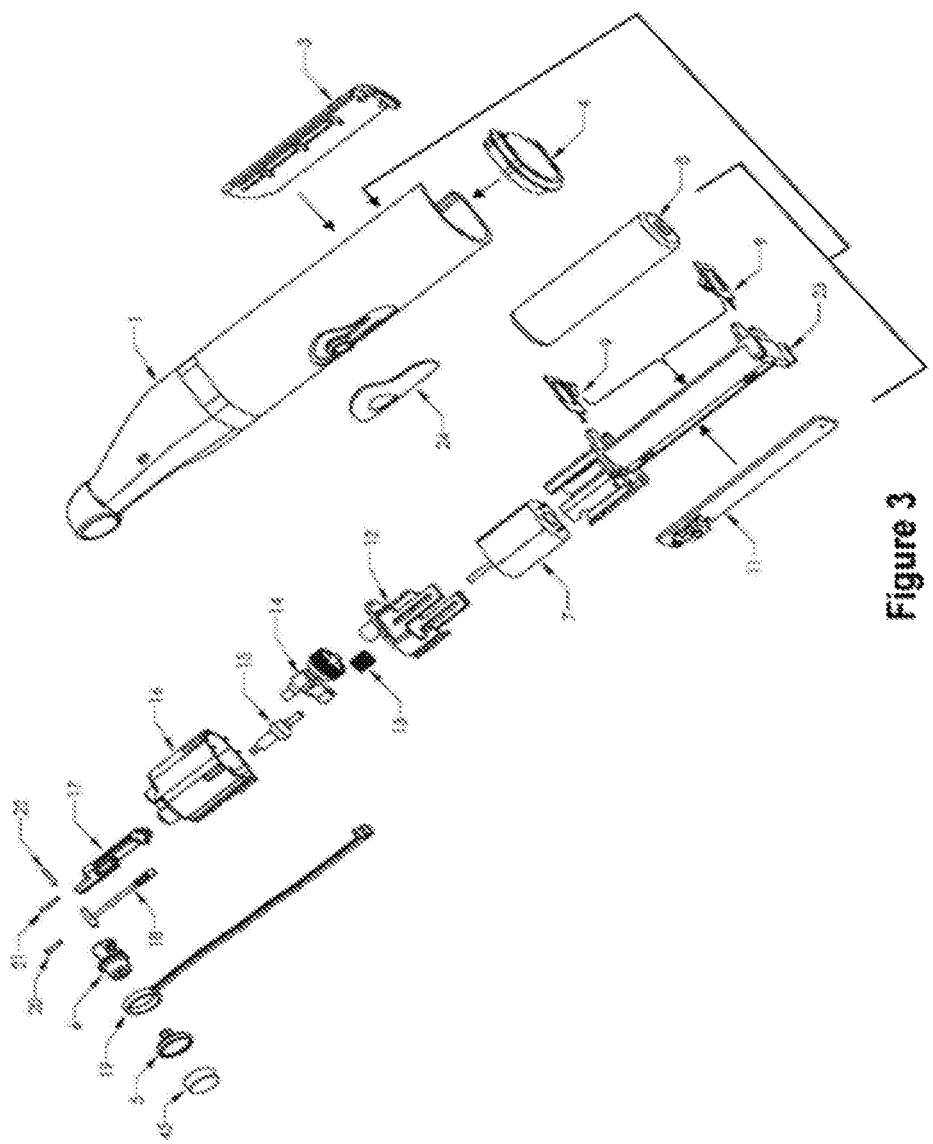
FIG. 3: Eyelid Care Appliance, Integral Version, Exploded View
Figure 6B:
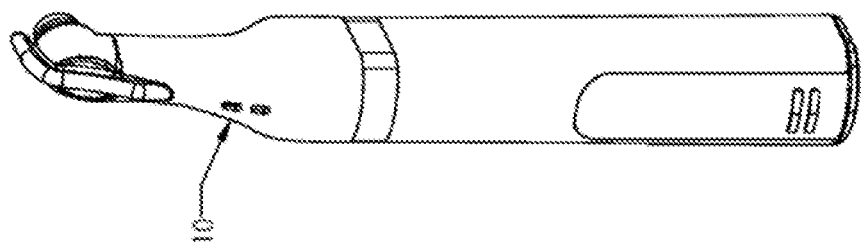
FIG. 6b: Eyelid Care Appliance, Integral Version, Suction Pump Embodiment, Rear Isometric View
Figure 6A:
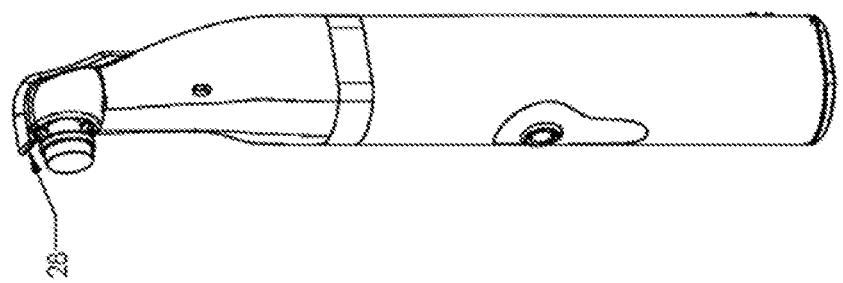
FIG. 6a: Eyelid Care Appliance, Integral Version Suction Pump Embodiment, Front Isometric View
Figure 5:
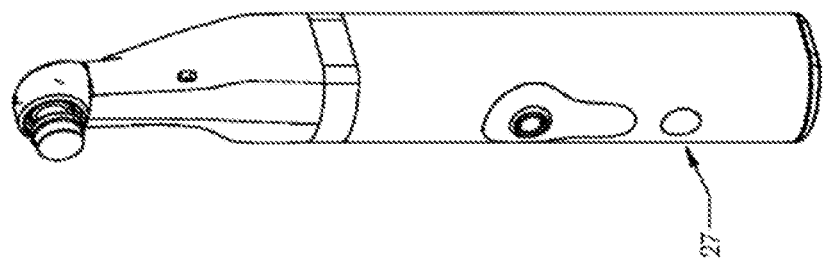
FIG. 5: Eyelid Care Appliance, integral Version, LED Embodiment with LED Light Ring and Adjustment, Front Isometric View
Figure 4:
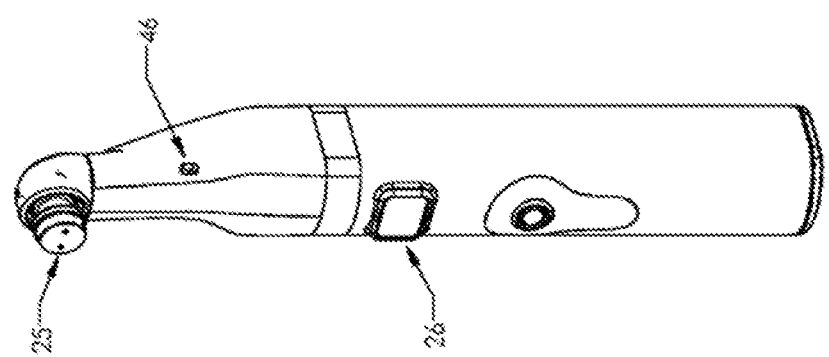
FIG. 4: Eyelid Care Appliance, Integral Version, LCD Embodiment, Front Isometric View
Figure 7B:
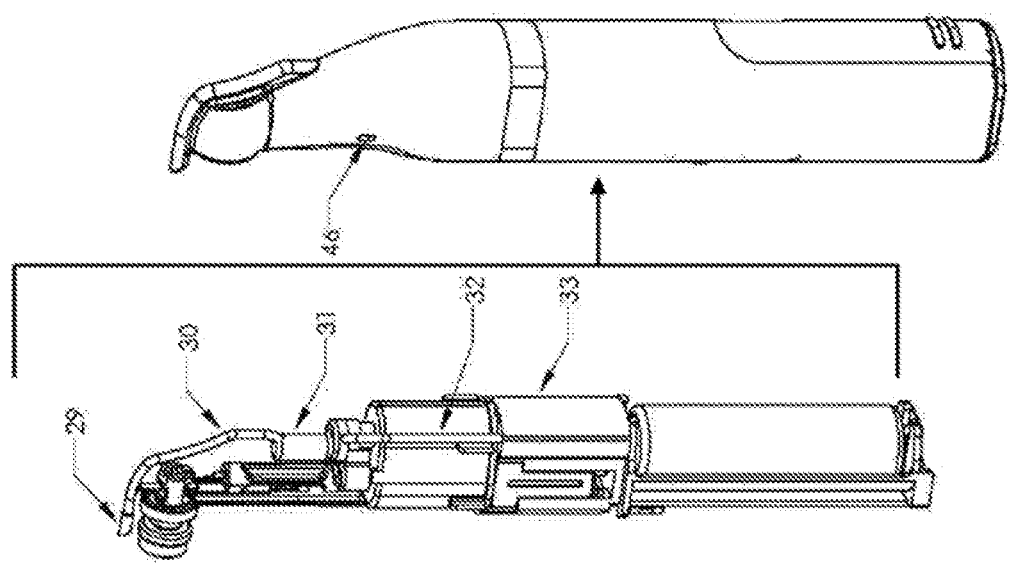
FIG. 7b: Eyelid Care Appliance, Integral Version, Liquid/Gas Pump Embodiment Exploded View
Figure 7A:
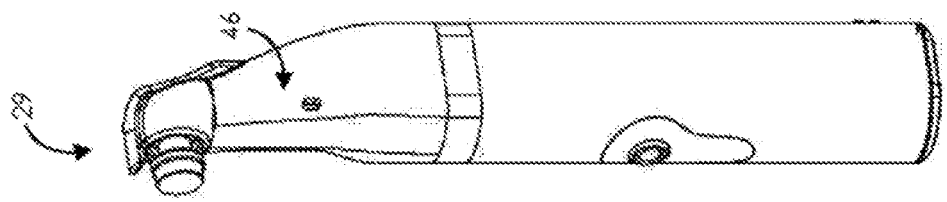
FIG. 7a: Eyelid Care Appliance, Integral Version, Liquid/Gas Pump Embodiment Front Isometric View
Figure 8C:
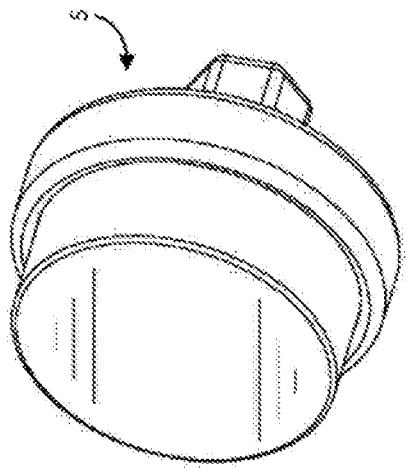
FIG. 8c: Cylindrical Spongehead Isometric View FIG. 9 Concave Spongehead Front View
Figure 9C:
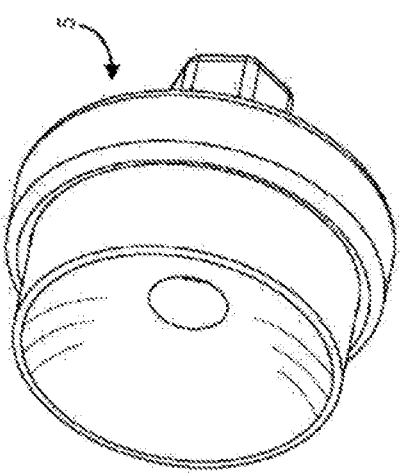
FIG. 9c: Concave Spongehead Isometric View
Figure 8B:
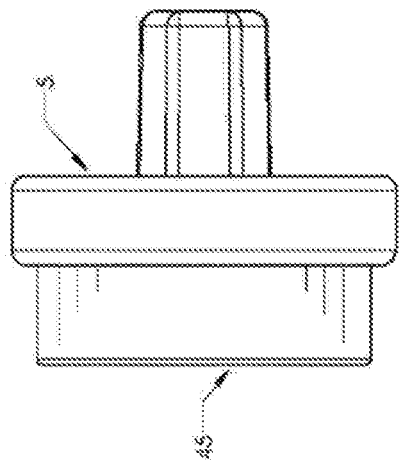
FIG. 8b: Cylindrical Spongehead Side View
Figure 9B:
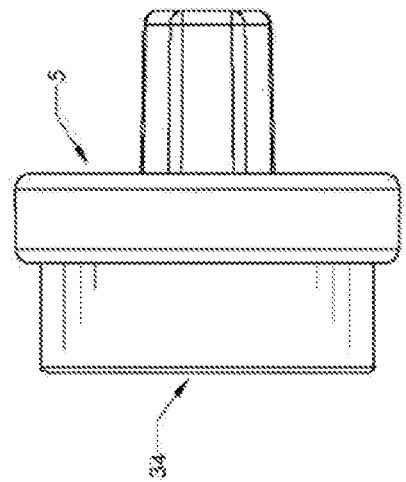
FIG. 9b: Concave Spongehead Side View
Figure 8A:
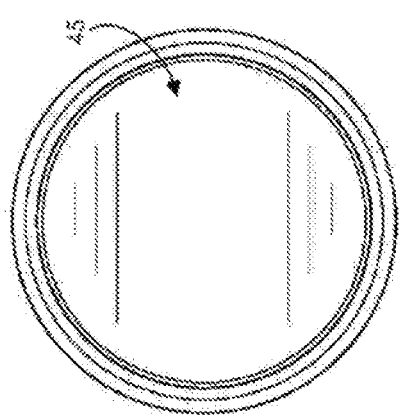
FIG. 8a: Cylindrical Spongehead Front View
Figure 9A:
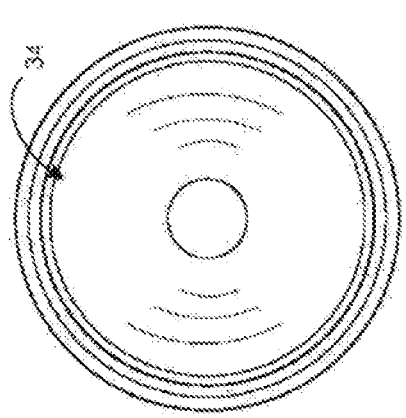
Figure 10C:
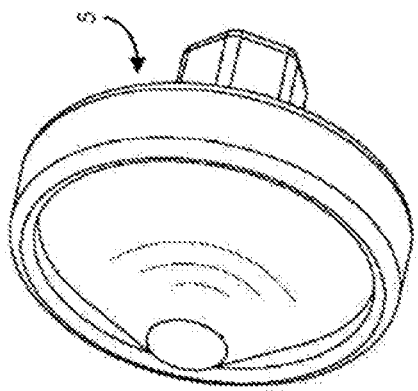
FIG. 10c: Pointed Spongehead Isometric View
Figure 11C:
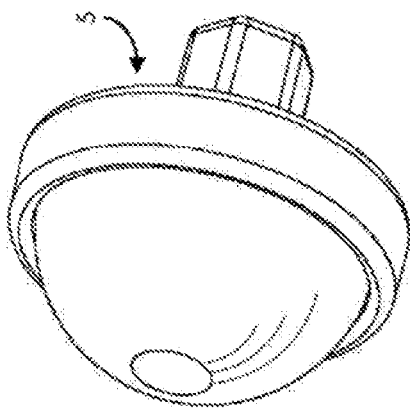
FIG. 11c: Convex Spongehead Isometric View
Figure 10B:
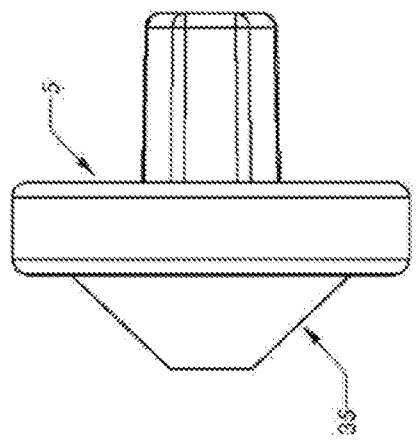
FIG. 10b: Pointed Spongehead Side View
Figure 11B:
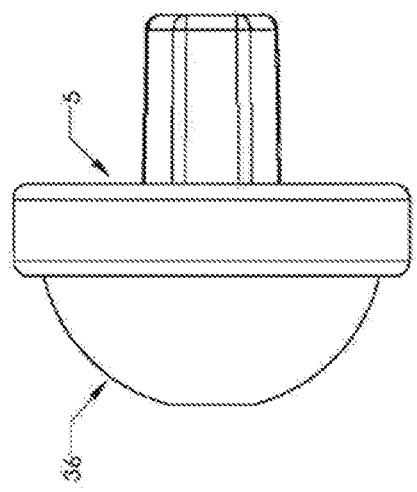
FIG. 11b: Convex Spongehead Side View
Figure 10A:
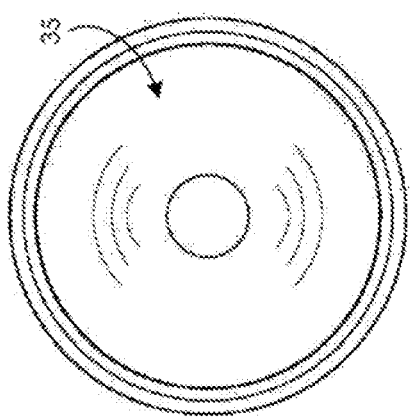
FIG. 10a: Pointed Spongehead Front View
Figure 11A:
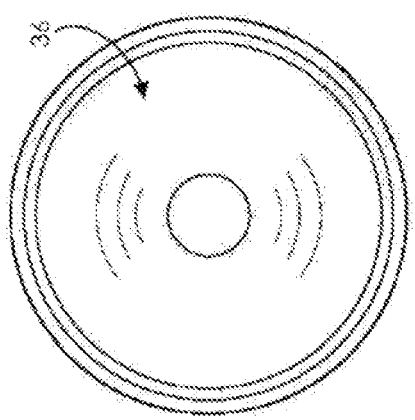
FIG. 11a: Convex Spongehead Front View
Figure 14C:
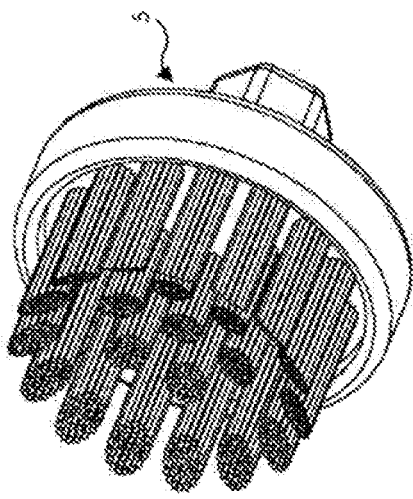
FIG. 14c: Concave Bristle Isometric View
Figure 15C:
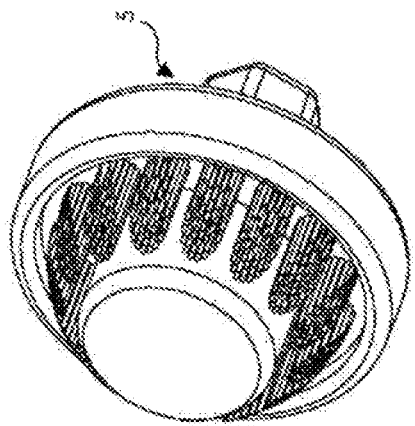
FIG. 15c: Convex Bristle Spongehead Isometric View
Figure 14B:
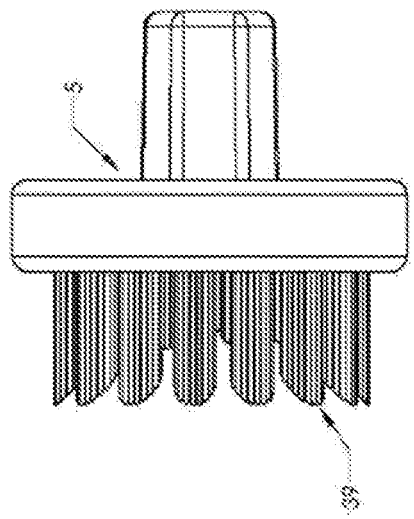
FIG. 14b: Concave Bristle Head Side View
Figure 15B:
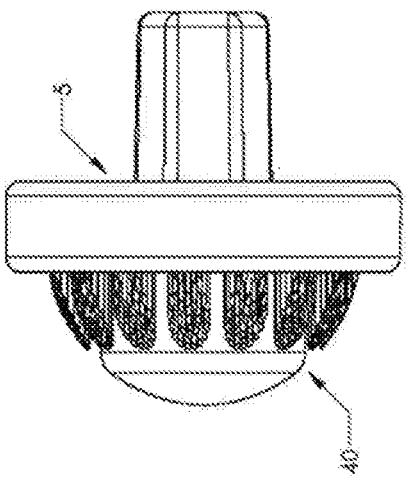
FIG. 15b: Convex Bristle Spongehead Side View
Figure 14A:
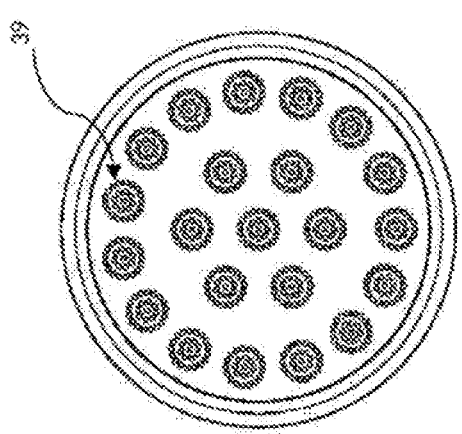
FIG. 14a: Concave Bristle Head Front View
Figure 15A:
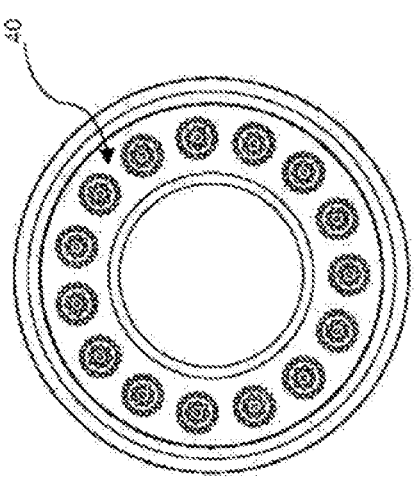
FIG. 15a: Convex Bristle Spongehead Front View

As shown in FIG. 2a, a sponge mount 5 bearing a sponge 45 is detachably (aka removably) affixed to the head receiver 6. The sponge mount 5 preferably has a polygonal post is inserted into a socket on the head receiver 6, The head receiver 6 is linked to the distal end of the drive system and driven in an oscillating motion by the drive system. The post/socket fastening system facilitates the easy attachment and removal of a spongehead. Disposable spongeheads are inexpensive, disposable, yet can be distributed sterile in packages. Multiple use spongeheads, for specific clinical procedures, are durable enough to withstand being autoclaved or otherwise repeatedly sterilized. The device of the invention has several alternative embodiments with fluid reservoirs of different types. The simplest design equipped with a fluid reservoir uses a head in which the sponge has a recessed tip (called a "concave spongehead", shown in FIGS. 9a-9c, with a concave sponge 34, which allows for liquids, gels and ointments deposited in the recess of the tip to be applied to the eyelid surface when the device of the invention is in use. Another embodiment of the device of the invention, as shown in FIGS. 7a and 7b, features a fluid reservoir 33 and a pump 31 and supply channel 30, 32 that connect the reservoir to a nozzle 29 near (or alternatively, ported through) the spongehead 2. Embodiments of the eyelid care appliance with reservoirs are equipped with dispensing controls and associated sensors, valves, and optional data channels that report sensor output and valve status. Controls in the eyelid care appliance are activated by buttons on the housing (or handpiece) and implemented by a processor on a printed circuit board 11 in FIG. 3) Liquids, gels, ointments, cleansers, solvents, gases, powders or other fluid or fluidizable medicaments are placed in the reservoir for delivery to or near the spongehead through the supply channel. The pump 31 forces the contents of the reservoir into or near the spongehead for dispersal on the eyelid being cleaned or treated. Dispensed fluids can include cleaning agents, Betadine, antiseptics, antimicrobials, anti-inflammatories, anesthetics, saline solution, water, solvents, taggants, stains, pharmaceuticals, nutriceuticals, and monoclonal antibodies. Reservoir and pump equipped embodiments can include a means to fluidize a powder or liquid into an aerosol for dispersal. An embodiment equipped to disperse liquids or gases can be equipped with a heater to heat the liquid or gas before dispersal near or through the spongehead. Another embodiment equipped to disperse gases can use ambient air, preferably filtered by a filter in the air intake, rather than gas in a reservoir; this embodiment is particularly useful for administration of aerosols, since separate gas reservoir is not needed. Heated fluids (liquid, gas, or air) can be used to warm the surface of the eyelid to "melt" blockages in meibomian glands, and the spongehead (oscillating or inactive) can be used to massage blockage areas. A "massage" spongehead would preferably have a convex sponge 36 (FIG. 10*b*) or conical sponge 43 (FIG. 17*b*).

The drive module of an eyelid care appliance is either (i) in the same housing 1 as an eyelid care module, or (ii) interfaced with a detachable neck and a coupler, to transmit oscillating motion to the head receiver. A two-piece appliance can have all the structural elements and functionality of an integral eyelid care appliance other than the neck being detachable from a handpiece (e.g., a battery powered toothbrush).

As shown in FIG. 3, a battery 8 is fitted in a battery housing 23 in the proximal end of the main housing 1. Battery access is through a battery door 3. The battery contacts battery clips 9 to supply DC motor 7 with electrical power with power controlled via printed circuit board 11 and a power button that is surrounded by a power button over-molding 24. Housing cap 4 seals the proximal end. A DC motor 7 with a pinion gear 13 on its output shaft drives a spur gear linkage 14 that converts rotary motion of the pinion gear 13 to oscillating (reciprocally arcuate) motion and drives a keyed shaft 15. Pinion gear 13, spur gear linkage 14 and keyed shaft 15 fit within a drive housing 16. Receiver linkage 17 transmits the oscillating motion of the keyed shaft 15 through a linkage tee with spring 18 to the head receiver 6. Housing pin 20, linkage pin 21, and carrier pin 22 join the assembly of receiver linkage 17, linkage tee with spring 18, and head receiver 6. Drive system adjustment holes 46 permit adjustment of the pins for proper orientation of head receiver 6. The sponge mount 5 with affixed sponge 45 fits firmly (either by friction or by detent) into a head receiver 6, and oscillates in a fixed relationship to the head receiver 6. Light pipe and light ring 19 provide light in the direction of the spongehead post axis from an LED mounted on and controlled by printed circuit board 11. Alternatively, power controlled by printed circuit board 11 can be provided to LEDs near the head receiver 6 or to LEDs on the distal portion of the eyelid care appliance. If a rechargeable battery is used as the power source in the handpiece, a battery charger (e.g., inductive, or conductive terminals) can be incorporated into a stand or holder for the device of the invention; alternatively, the battery can be removed through battery cover 3 for recharging in a charging dock. One or more lighting LEDs can project light in front of the spongehead, thereby providing adequate illumination for the user and/or a video camera.

As shown in FIG. 19, alternative embodiments of the eyelid care appliance include designs in which the appliance has a "pistol grip" proximal portion and adjustable head angle 47. Other alternative embodiments include (i) a "pistol grip" handpiece, (ii) versions in which the eyelid care appliance mounted on or integral with a glove, or (iii) in which the eyelid care appliance is mounted on a handstrap. The pistol grip integral embodiments can include a distal pivot so that the angle between the grip portion and the distal portion containing the eyelid care module (or in two-piece embodiments, the angle between the handpiece and the detachable neck) can be selected by the user and maintained by detents in the pivot mechanism or by a lock.

As shown in FIG. 4 (showing sensor 25), FIG. 5 (showing LED control 27), FIG. 6*a* (showing suction nozzle 28), 6*b* (showing suction pump outlet 10), and FIGS. 7*a* and 7*b* (showing liquid/gas nozzle 29, liquid/gas tubing 30, 32, liquid/gas pump 31, and liquid/gas reservoir 33), various sensors, inlets, and outlets can be configured in the eyelid care appliance. FIG. 4 shows a suction pump with a suction inlet near the spongehead and an suction pump outlet 10 in the housing, wherein the suction inlet removes debris and liquids from the eyelid margin and expels such debris and liquids as a wastestream through the outlet 10 in the housing. The outlet 10 can be configured with a connector and mated with connectorized tubing that routes the wastestream into a collection reservoir, diagnostic apparatus input, or a drain. A preferred embodiment further comprises a suction pump with a suction inlet near the spongehead and an outlet in the housing, wherein the suction inlet removes debris and liquids from the eyelid margin and expels such debris and liquids as a wastestream through an outlet in the housing. In embodiments with a suction pump, the wastestream input or output of the suction pump can be examined by a video camera, flow cytometer, or other sensor and associated software to detect and report the contents of the wastestream, e.g., particle count, chemical profile (before cleaning, during cleaning, after cleaning, esp. of tear film), presence of bacteria, etc. Stains, monoclonal antibodies, and other taggants can be administered and monitored as part of wastestream assays. A preferred embodiment further comprises a suction pump with a suction inlet, near the spongehead and an outlet in the housing, wherein the suction inlet removes debris and liquids from the eyelid margin and expels such debris and liquids as a wastestream through an outlet in the housing and wherein the wastestream input or output of the suction pump is examined by a video camera, flow cytometer, or other sensor and associated software to detect and report the contents of the wastestream. This embodiment provides the first real-time reporting of tear film profile, the efficacy of eyelid cleaning, cleanser concentration, medicament concentration, etc., and provides a very important new tool in training, in diagnosis, and in monitoring therapeutic interventions.

As shown in FIGS. 8*a* through 17*c*, the sponge or other material mounted on a spongehead for contact with a skin or wound surface can have various constituent materials and geometries adapted to the cleaning, therapeutic application, or assay to be conducted. Exemplary materials and geometries are concave spongehead 34, pointed spongehead 35, convex spongehead 36, bristle head 37, bristle spongehead 38, concave bristle head 39, convex bristle spongehead 40, small, higher chamfer spongehead 41, small, higher chamfer sponge mount 42, and conical spongehead 43.

Software applications and sensors used with embodiments of the eyelid care appliance (including embodiments with a system on a chip within the eyelid care appliance or with a smart device linked by NFC to the eyelid care appliance) can detect and report how often and for how long one has scrubbed an area, battery condition, how much pressure is applied at the spongehead, patency of the meibomian glands, health of the eyelid margin, etc. A video and/or sensor equipped eyelid care appliance can also provide images and/or assay reports, respectively, of other body surfaces, e.g., skin lesions, wounds. The software applications can run on a computer integral with the eyelid care appliance, on a remote device, or on networked devices, including the eyelid care appliance as a client in a network.

Embodiments of the invention with lighting and a video proximity system can be equipped with band-limited light sources, either by selection of LED emitters and/or by filtering, and with multispectral image analysis software. Such an embodiment further comprises one or more band-limited light sources that project light in front of the spongehead, wherein the proximity system is a video camera with lens mounted near the spongehead and in near field communication with a smart device, wherein the video output from the video camera is fed to multispectral image analysis software in the smart device or in the appliance, and the output of the multispectral image analysis software is displayed on the smart device. Using multispectral image analysis well known in the art, and implemented in software applications running on an integral processor or on a smart device with an NFC link to the eyelid care appliance, provides a non-invasive, real-time method of determining the health of an eyelid (or other skin area).

Although a sponge cover can be made to fit over an existing brush head of a powered toothbrush, and a "sponge cover" is less expensive than a spongehead, the safety of use of a sponge cover depends upon how securely the sponge cover is attached or adhered to the brush head and the size of the brush head. Moreover, electric toothbrush brush heads are generally far too big, and the handpiece too cumbersome, for use in eyelid care.

In addition to routine eyelid cleaning, SA Cleaning, and SP Cleaning, the invention may also be used to clean other areas and types of tissue where, or in other applications in which, a surface needs to be thoroughly cleaned, such as:

a. Pre-operative eyelid cleaning for ocular or pen-ocular surgery with cleansing/antimicrobial solutions (including povodine/iodine solution).

b. Application of dermatologic creams for acne to be applied directly to the blemish or other skin area. This will allow a more precise placement of the medication so as not to dry out surrounding skin. Also, the oscillating sponge will allow a more even and thorough application of the product. The sponge can be pre-loaded with an appropriate amount of medication. Sensor-equipped embodiment of the invention can provide assay reports of the skin area.

c. Application of eyelash lengthening therapies, e.g., the Latisse® (Allergan Corp.) therapy currently recommends the use of small applicator brushes to apply the product. This demands very exact eye-hand coordination. Use of the invention, preferably a video-equipped embodiment, would allow easier application with perhaps better coverage of the lashes.

d. Wound cleaning and debridement. Wound cleaning and debridement can be challenging by existing manual techniques. This device can be used to thoroughly and precisely clean wounds and removal foreign material and dead tissue from a wound. Sensor-equipped embodiment of the invention can provide assay reports of the skin area.

e. To apply a pharmaceutical to a lesion. Sensor-equipped embodiment of the invention can provide assay reports of the skin area.

f. Veterinary use for cleaning eyelids or other areas on animals that require a small cleaning device. Sensor-equipped embodiment of the invention can provide assay reports of the skin area.

The eyelid care appliance can be made in various sizes, e.g., pediatric and adult. An eyelid care appliance can be made in various sizes of drive module, e.g., different glove sizes, different pistol grip sizes, and in different sizes of spongehead, e.g., pediatric and adult. Two-piece embodiments of the eyelid care appliance can be made with a standard interface between detachable neck and handpiece so that different sizes of detachable necks can be mated with different sizes of handpieces. Any embodiment of the eyelid care appliance can include an accelerometer that detects that the appliance has been dropped and that causes the motor to be powered off. Any embodiment of the eyelid care appliance can also use NFC to report its location to a smart device.

Alternative embodiments of the invention designed to care for body surfaces other than eyelids are called herein "surface care devices" and, like eyelid care appliances, comprise a drive module and an eyelid care module, and include the alternative embodiments described above (e.g., proximity systems, fluid and fluidized agent dispersal systems, suction systems, NFC links to smart devices, etc.). Spongeheads of various diameters and topologies are tailored to the skin area to be treated, e.g., a large concave spongehead to treat elbows, a small concave spongehead to treat fingertips. Surface care devices also include wound care devices adapted for various types of wounds to be cleaned or otherwise analyzed or treated using a surface care device; one embodiment of a surface care device for wounds is a mechanical debridement device.

A surface care appliance can be used for pre-operative scrubbing of small areas of skin before surgery, in particular for scrubbing of eyelid margins. Pre-operative scrubbing is currently done manually with swabs and sponges.

An alternative embodiment of the invention can be configured by choice of spongehead to dean makeup off eyelids; a sterile spongehead could be mounted for each use. Current methods of using moistened towellettes or cotton balls may not thoroughly dean eyelids of all residual makeup. This device could be used either primarily or as an adjunct to the above described methods to more thoroughly and rapidly remove eye makeup.

An alternative embodiment of the invention can be configured by choice of spongehead to clean, buff or polish nails and for cuticle care. Current techniques use reusable, manual devices which are of questionable sterility. This embodiment would provide a quicker, more efficient way to perform nail and cuticle tasks, and a sterile spongehead could be mounted for each use.

To generalize the preceding description, like eyelid care appliances, surface care devices of the invention are of two types: (1) an integral appliance, with an eyelid care module and drive module within a single housing, optionally with a pivoted grip, or (2) a two-piece appliance, comprising a handpiece and detachable neck, optionally with a pivoted handpiece. Embodiments of surface care devices, e.g., for skin care and wound care, are adapted for areas to be cleaned or otherwise analyzed or treated.

Further modifications will also suggest themselves to those skilled in this art, and such are considered to fall within the spirit and scope of the invention as defined in the appended claims.

What is claimed is:

1. A method of cleaning the eyelid margins and meibomian gland orifices of cellular and sebaceous debris comprising of the steps:
 a. attaching a brush head to an eyelid care appliance;
 b. said brush head having a primary axis through the center of a face of the brush head;
 c. said eyelid care appliance having a drive system that transmits motive force to oscillate said brush head;

d. said drive system having a proximity sensor, proximity controls and proximity annunciator;
e. turning on said drive system and said proximity controls and said proximity controls comprising of and on and off control;
f. accessing the glands of the eyelid with said brush head;
g. said drive system having an oscillation frequency which oscillates said brush head and said oscillation comprises repeating circular rotation up to a first angular amount in a first direction around the axis of the head, and circular rotation up to a second angular amount in a second opposite direction around the primary axis of the head such that the head does not make a full revolution;
h. contacting said distal surface of said brush head to the outer surface of the eyelids to clean said eyelid margins and said meibomian gland orifices;
i. said proximity sensor monitoring said eyelid margins and said meibomian gland orifices; and
j. said proximity sensor monitoring said eyelid margins and said meibomian gland orifices and said proximity annunciator sends an audible tone that reflects the distance between said brush head and said eyelid margins.

2. The method of claim 1, wherein the said brush head has a proximal surface with a center and distal surface with a center, said primary axis passing thru the center of said brush head said proximal surface and said distal surface and said distal surface of said brush head contacting said eyelid margins.

3. The method of claim 1, wherein said brush head material is selected from the group consisting of low-density polyether, polyvinyl alcohol and polyester.

4. The method of claim 1, wherein the eyelid care appliance comprises a power supply, a motor, a head receiver, motor controls, and a proximity sensing system.

5. The method of claim 1, wherein said oscillation frequency of said brush head is 7,000 to 40,000 strokes per minute.

6. The method of claim 1, wherein a circumference of said brush head is circular around said primary axis such that the circular rotation is around said primary axis and spins back and forth in first direction and then in a second direction around said primary axis.

7. The method of claim 1, wherein said proximity sensor is a video camera.

8. The method of claim 1, wherein said video annunciator is a video camera and smartphone.

9. The method of claim 1, wherein said proximity controls is a video camera and smartphone.

* * * * *